(12) United States Patent
Wertz et al.

(10) Patent No.: US 7,041,489 B2
(45) Date of Patent: May 9, 2006

(54) RECOMBINANT RESPIRATORY SYNCYTIAL VIRUSES WITH DELETED SURFACE GLYCOPROTEIN GENES AND USES THEREOF

(75) Inventors: Gail W. Wertz, Birmingham, AL (US); Alexander George Megaw, Glasgow (GB); A. Tom Oomens, Birmingham, AL (US)

(73) Assignee: The UAB Research Foundation, Birmingham, AL (US)

( * ) Notice: Subject to any disclaimer, the term of this patent is extended or adjusted under 35 U.S.C. 154(b) by 123 days.

(21) Appl. No.: 10/262,238

(22) Filed: Oct. 1, 2002

(65) Prior Publication Data

US 2003/0072773 A1    Apr. 17, 2003

Related U.S. Application Data

(60) Provisional application No. 60/397,289, filed on Jul. 19, 2002, now abandoned, provisional application No. 60/326,259, filed on Oct. 1, 2001, now abandoned.

(51) Int. Cl.
*C12N 7/00* (2006.01)

(52) U.S. Cl. .................................. 435/235.1; 435/320.1

(58) Field of Classification Search ............. 435/235.1, 435/320.1
See application file for complete search history.

(56) References Cited

U.S. PATENT DOCUMENTS

| 5,716,821 A | 2/1998 | Wertz et al. |
| 5,789,229 A | 8/1998 | Wertz et al. |
| 2002/0146433 A1* | 10/2002 | Krempl et al. ........... 424/204.1 |

* cited by examiner

*Primary Examiner*—James Housel
*Assistant Examiner*—Myron G. Hill
(74) *Attorney, Agent, or Firm*—Schwartz Sung & Webster

(57) ABSTRACT

The present invention provides recombinant respiratory syncytial viruses (RSV) in which all of the surface glycoprotein genes encoding the attachment protein G, the fusion protein F, and the Small Hydrophobic protein SH are deleted. The genes are replaced by a chimeric gene encoding a heterologous entry protein derived from the Vesicular Stomatitis Virus G protein or GP64 of baculovirus. Alternatively, the replacement proteins are provided in trans. Marker genes such as those encoding β-glucuronidase (GUS) and green fluorescent protein (EGFP) are also added to the upstream and downstream side of the hybrid gene for easy detection. These infectious recombinant respiratory syncytial viruses offer alternatives and improvements as vaccine candidates.

5 Claims, 15 Drawing Sheets

```
                              Xba I
         .....CAT CTT TGC ATT AAA|tct|AGA AGC ACA CCA ......TTT AGT AAC TAA
G^VSV    .....his leu cys ile lys|ser|arg ser thr pro ...... phe ser asn  *
         ......487 488 489 490 491|   |553 554 555 556 ...... 572 573 574

VSV G  ⇐|  |⇒  RS virus F
```

Fig. 1C

RS$_{\Delta SH}$,G/G$^{VSV}$

RECOMBINANT RESPIRATORY SYNCYTIAL VIRUSES WITH DELETED SURFACE GLYCOPROTEIN GENES AND USES THEREOF

CROSS-REFERENCE TO RELATED APPLICATION

This non-provisional patent application claims benefit of provisional patent applications 60/397,289, filed Jul. 19, 2002, now abandoned and U.S. Ser. No. 60/326,259, filed Oct. 1, 2001, now abandoned.

FEDERAL FUNDING LEGEND

This invention was produced in part using funds from the Federal government under NIH grant AJ20182. Accordingly, the Federal government has certain rights in this invention.

FEDERAL FUNDING LEGEND

This invention was produced in part using funds obtained from a grant from the National Institutes of Health. Consequently, the federal government has certain rights in this invention.

BACKGROUND OF THE INVENTION

1. Field of the Invention

The present invention relates generally to the fields of molecular virology and vaccine development. More specifically, the present invention provides recombinant respiratory syncytial viruses in which the genes encoding the attachment protein G, the fusion protein F, and the Small Hydrophobic protein SH were deleted and replaced by a foreign/heterologous gene or in which the individual gene products or foreign/heterologous gene products were provided in trans.

2. Description of the Related Art

Human respiratory syncytial virus (HRSV) is a major cause of severe lower respiratory tract disease in infants and children worldwide as well as in immunosuppressed individuals and the elderly (Pringle, 1987; Couch et al., 1997; Han et al., 1999). Amidst ongoing efforts to develop human respiratory syncytial virus specific vaccines and therapeutic agents, prevention and treatment of human respiratory syncytial virus disease remain a significant challenge. Human respiratory syncytial virus is the type species of the genus *Pneumovirus* within the family Paramyxoviridae and contains a negative-sense, single-stranded RNA genome of 15,222 nucleotides that expresses eleven known proteins from ten genes (Huang and Wertz, 1983; Collins et al., 1984). Three proteins, SH (small hydrophobic), G (attachment), and F (fusion), have been characterized as transmembrane glycoproteins and are detected in purified virions (Anderson et al., 1992; Huang et al., 1985). On the surface of infected cells, the G and F proteins concentrate in cell-associated, virus-induced filamentous structures with variable lengths of up to 10 μm (Bächi and Howe, 1973; Fuchs and Bächi, 1975; Roberts et al., 1994; Buchholz et al., 2000; Stope et al., 2001).

The SH protein is a small integral membrane protein of unknown function, with a relatively low amino acid conservation among human respiratory syncytial virus strains (Collins and Wertz, 1985; Collins et al., 1990). Previous studies indicate that SH is dispensable for human respiratory syncytial virus growth in cell culture, and its absence has little impact on the ability of the virus to replicate in the respiratory tracts of mice and chimpanzees (Bukreyev et al., 1997; Karron et al., 1997; Whitehead et al., 1999; Techaarpornkul et al., 2001).

The G gene of human respiratory syncytial virus expresses both a type II membrane-anchored glycoprotein and a soluble protein (Wertz et al., 1985, 1989; Hendricks et al., 1987; Roberts et al., 1994). G protein is heavily O-glycosylated and shows significant structural similarities to mucinous proteins (Wertz et al., 1985, 1989). The G protein was initially characterized as providing an attachment function (Levine et al., 1987), and domains in G have since been identified that bind to sulfated glycosaminoglycans on the cell surface in vitro (Feldman et al., 1999; Martinez and Melero, 2000). The requirement for G protein in infectivity in cell culture varies depending on the cell type. Both a cold-adapted virus in which most of the sequence encoding the SH and G proteins is absent, and a n engineered virus lacking the G gene replicate efficiently in Vero cells. However, replication of these G-deleted viruses is significantly impaired in HEp-2 cells as well as in mice, cotton rats, and humans (Karron et al., 1997; Teng et al., 2001).

The fusion protein, F, is a type I transmembrane glycoprotein that mediates the formation of syncytia typically observed in human respiratory syncytial virus infected cells (Walsh and Hruska, 1983). F protein is thought to direct entry of human respiratory syncytial virus at the plasma membrane in a pH-independent manner (Srinivasakumar et al., 1991). Among the transmembrane glyoproteins, F appears to be a critical component for virus transmission, as F, matrix (M) protein, and the nucleocapsid were found to be the minimal requirements for production of infectious particles, and viruses that express F as the only glycoprotein propagated efficiently in Vero cells (Karron et al., 1997; Teng and Collins, 1998; Techaarpornkul et al., 2001; Teng et al., 2001).

The G and F proteins contain the major antigenic epitopes of human respiratory syncytial virus, and their roles in the antihuman respiratory syncytial virus virus immune response have been investigated extensively (Wertz et al., 1987; Stott et al., 1987; Murphy et al., 1990; Tripp et al., 1999; Sullender, 2000; Graham et al., 2002; Varga and Braciale, 2002). In contrast, relatively few studies have addressed the roles of SH, G, and F in viral entry, assembly, and transmission. In addition to the SH and G deletion studies described above, glycoprotein substitution studies with bovine respiratory syncytial virus (BRSV) showed that the human respiratory syncytial virus G and F proteins could functionally replace their homologs in BRSV, and that the bovine parainfluenza virus (BPIV) HN and F proteins could functionally replace the BRSV G and F proteins (Buchholz et al., 1999; Stope et al., 2001). However, to date infectious human respiratory syncytial viruses lacking an F gene from the Paramyxoviridae family have not been reported.

Current work to develop a safe and effective vaccine against respiratory syncytial virus is developing rapidly and it is now possible to recover respiratory syncytial virus from cDNA clones and to engineer viruses to specification. However, previous vaccine attempts with killed vaccine revealed that vaccination resulted in a n inappropriate immune response that led to more severe disease upon challenge. The cause of this phenomenon has not been clearly elucidated. Attempts to dissect the problem have been made with isolated viral components but not within the context of an infectious virus.

Thus, the prior art is deficient in the lack of improved recombinant respiratory syncytial viruses useful for the testing and development of vaccine for respiratory syncytial virus. The present invention fulfills this long-standing need and desire in the art.

SUMMARY OF THE INVENTION

To examine the requirements of the human respiratory syncytial virus SH (small hydrophobic), G (attachment), and F (fusion) proteins for virus infectivity and morphology, the prototype A2 strain of human respiratory syncytial virus was used to generate a series of cDNAs from which 1) the SH open reading frame (ORF), 2) the SH and G ORFs, or 3) the SH, G and F open reading frames were deleted. The deleted SH open reading frame was replaced with that of a marker such as green fluorescent protein. The G open reading frame was replaced with that of $G^{vsv}$, a chimeric glycoprotein consisting of the Vesicular stomatitis Indiana virus (VSIV) G protein ecto and transmembrane domains coupled to the human respiratory syncytial virus F cytoplasmic tail. In addition to VSIV G protein, GP64 of baculovirus can also be used. GP64 is a baculovirus trimeric membrane fusion protein functionally similar to, but evolutionarily distant from the VSIV G protein. The F ORF was replaced with that of marker protein β-glucuronidase.

The number of genes and all the intergenic junctions in these constructs were kept as found in A2 virus in order to maintain authentic levels of transcription. Addition of marker genes keeps the number of genes in the viral genome constant and the number of transcriptional attenuation steps the same so that the expression levels of all genes located downstream of any potential deletions will not be altered from that of the wild type. These marker genes can be included or not as desired, but omitting them and changing the gene count will have effects on downstream transcription.

Infectious viruses were recovered from all three engineered cDNAs and designated RSΔSH, RSΔSH,G/$G^{vsv}$, and RSΔSH,G,F/$G^{vsv}$ respectively. Low pH-induced syncytium formation was observed in cells infected with viruses RSΔSH,G/$G^{vsv}$ and RSΔSH,G,F/$G^{vsv}$, indicating that $V^{SV}$ was expressed and functional. Neutralization of infectivity by anti-VSIV G antibodies and inhibition of entry by ammonium chloride showed that RSΔSH,G,F/$G^{vsv}$ infectivity was mediated by $G^{vsv}$ and that an acidification step was required for entry into the host cell, similar to VSIV virions. All three engineered viruses displayed growth kinetics and virus yields similar to a wt A2 virus both in Vero and HEp-2 cells. Abundant virus-induced filaments were observed at the surface of cells infected with each of the three engineered viruses or with virus A2, indicating that neither the SH and G proteins, nor the F protein ecto- and transmembrane domains were required for the formation of these structures. This is the first report of the recovery of an infectious human respiratory syncytial virus lacking a Paramyxoviridae fusion protein and of manipulation of the human respiratory syncytial virus entry pathway via incorporation of a non-paramyxoviral transmembrane glycoprotein.

These data demonstrate that a single, heterologous glycoprotein can replace both the attachment and membrane fusion functions of the native respiratory syncytial virus glycoproteins G and F. Respiratory syncytial virus can use an alternate, low pH-mediated entry route in cell culture. Moreover, these data shows that beyond attachment and the fusion event upon its natural entry at the plasma membrane, SH, G, and F are not essential for the progression of respiratory syncytial virus infection in individually infected cells.

In one embodiment of the present invention, there is provided a recombinant respiratory syncytial virus (RSV) in which all of the surface glycoprotein genes encoding the attachment protein G, the fusion protein F, and the Small Hydrophobic protein SH are deleted and replaced by a chimeric gene encoding a heterologous protein that mediates cell infection and fusion activity of the respiratory syncytial virus.

In another embodiment of the present invention, there is provided a method of making a recombinant respiratory syncytial virus (RSV) that can infect a cell but cannot spread beyond said cell, comprising the steps of: deleting the genes encoding the attachment protein G, the fusion protein F, and the Small Hydrophobic protein SH, and providing in trans a heterologous protein that mediates cell infection of said respiratory syncytial virus.

In yet another embodiment of the present invention, there is provided a method of targeting a recombinant respiratory syncytial virus (RSV), comprising the steps of: deleting the genes encoding the G, F, and SH proteins, and replacing the deleted genes with a gene encoding a heterologous protein that mediates cell infection and targeting of said respiratory syncytial virus.

In another embodiment of the present invention, there is provided a method of testing immunogenicity of an epitope of the surface glycoprotein of respiratory syncytial virus (RSV) in a background of a live and transmissible virus, comprising the steps of: deleting the genes encoding the G, F, and SH proteins, and replacing the deleted genes with a gene encoding said epitope.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 1A shows composition of human respiratory syncytial virus cDNA with a modified gene content in genome positions six, seven, and eight: 1) pRSΔSH lacks the SH ORF and contains instead a GFP ORF; 2) pRSΔSH,G/$G^{vsv}$ lacks the SH and G ORFs which are replaced with those encoding GFP and $G^{vsv}$ respectively; 3) pRSΔSH,G,F/$G^{vsv}$ lacks all three transmembrane glycoprotein ORFs SH, G, and F and these were replaced with ORFs encoding GFP, $G^{vsv}$, and GUS respectively. The genomic sequences in these cDNAs are flanked by a T7 promoter (T7) and an HDV self-cleaving ribozyme sequence (HDV) followed by a T7 terminator sequence (ø). In the presence of T7 polymerase, a transcript corresponding to the human respiratory syncytial virus anti-genome is produced. Sizes of the engineered viral genomes are indicated on the right (nt=nucleotides). NS1/2, nonstructural proteins 1 and 2; N, nucleocapsid protein; P, phosphoprotein; M, matrix protein; M2, transcription factor; L, large polymerase; Le, leader; Tr, trailer.

FIG. 1B shows the strategy used for the generation of genetically modified viruses. A plasmid was generated that contained a cDNA of the prototypic human respiratory syncytial virus A2 strain but lacking the SH-G-F region (pRSΔSH,G,F). A shuttle vector containing introduced restriction sites, but in which gene junctions remained unaltered from the A2 virus (pBLS-6,7,8), was used to place selected ORFs in the sixth, seventh, and eighth genome positions within engineered cDNAs (utr, untranslated region; ge, gene end; ig, intergenic region; gs, gene start).

FIG. 1C shows $G^{vsv}$ is a chimeric viral membrane glycoprotein consisting of the VSIV G ecto and transmembrane domains (amino acids 1 to 491) coupled to the cytoplasmic tail domain of human respiratory syncytial virus F protein (amino acids 553 to 574) via an XbaI site, created by introduction of 3 nt (tct).

FIG. 10 shows multi-step growth curves of RSΔSH,G,F/$G^{bac}$ in Vero 76 cells at 37° C. or 33° C.

FIG. 11 shows multi-step growth curves of RSΔSH,G,F/$G^{bac}$ in HEp-2 cells at 37° C. or 33° C.

DETAILED DESCRIPTION OF THE INVENTION

Figure 2:
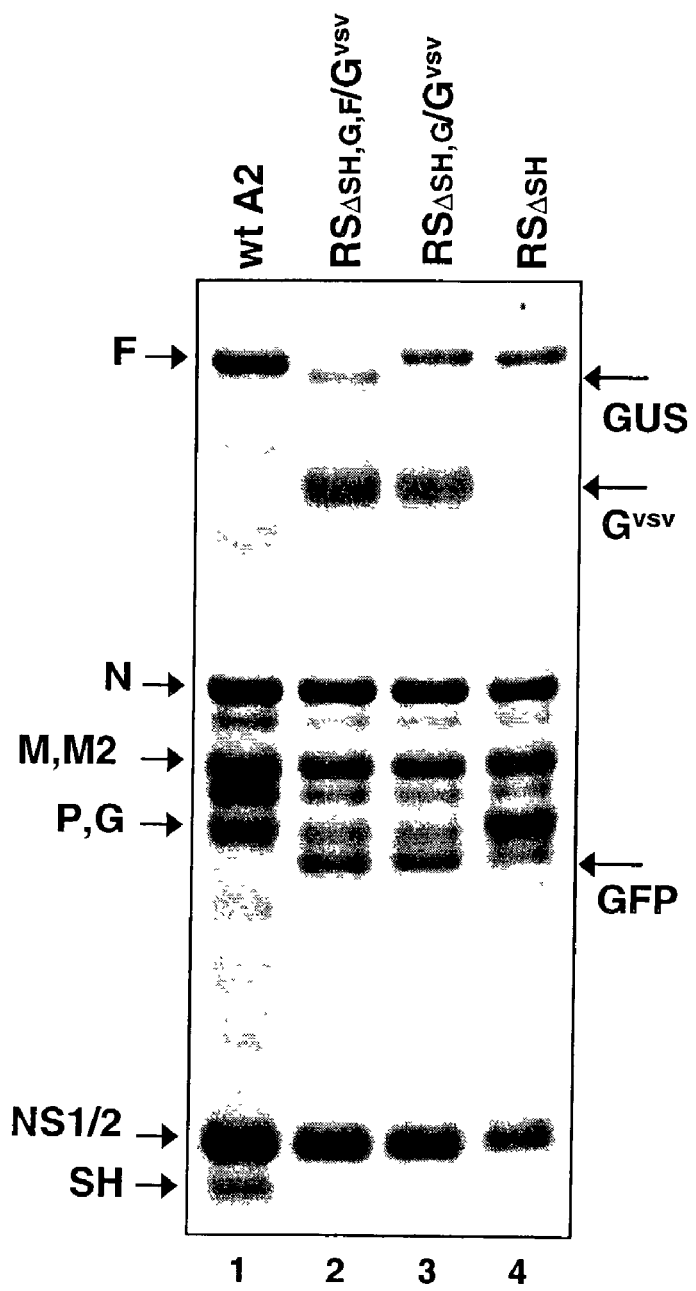
FIG. 2 shows RNA synthesis by the engineered viruses. Vero cells infected with the engineered viruses or virus A2 were subjected to metabolic labeling with $^3$H-uridine in the presence of actinomycin-D. Total RNA was isolated, 3' poly(A) tails removed by digestion with RNAse H following annealing with oligo-dT, and RNAs analyzed by agarose-urea gel electrophoresis. On the left, previously characterized monocistronic mRNAs from wt RS virus are indicated. On the right, the positions of transcripts from genes containing introduced ORFs $G^{vsv}$, GFP, and GUS are indicated. Lane 1, wt A2; lane 2, RSΔSH,G,F/$G^{vsv}$; lane 3, RSΔSH, G/$G^{vsv}$; lane 4, RSΔSH.

The recovery of human respiratory syncytial virus and bovine respiratory syncytial virus (BRSV) lacking the SH gene or SH and G genes combined has been reported previously (Bukreyev et al., 1997; Karron et al., 1997; Whitehead et al., 1999; Buchholz et al., 2000; Techaarpornkul et al., 2001; Teng et al., 2001; Karger et al., 2001). Also, G and F genes of bovine respiratory syncytial virus were successfully co-substituted with the bovine parainfluenza virus attachment and fusion protein genes (Stope et al., 2001). These engineered viruses all retained a functional Paramxoviridae fusion protein gene.

In contrast, the present invention discloses deleting the open reading frames (ORFs) of all three transmembrane glycoprotein genes SH, G and F simultaneously, and replacing them with three open reading frames encoding two marker proteins and a single chimeric transmembrane glycoprotein $G^{vsv}$ consisting of the Vesicular Stomatitis Virus (VSV) G protein ecto and transmembrane domains coupled to the respiratory syncytial virus F cytoplasmic tail domain (CTD). This strategy allowed the generatation of a respiratory syncytial virus that was independent of all its homologous transmembrane glycoproteins as a first step to develop a system to further examine the roles and requirements of SH, G, and F in the virus life cycle. It also allowed the examination of whether pseudotyping with a non-paramyxoviral membrane glycoprotein could be used as an approach to manipulate respiratory syncytial virus infectivity and transmission.

The present invention also provides recombinant respiratory syncytial virus that lacked the SH, G and F proteins and transmitted in cell culture by a hybrid protein derived from *Autographa californica* Multicapsid Nucleopolyhedrovirus (AcMNPV) GP64 protein. GP64 is a baculovirus trimeric membrane fusion protein functionally similar to, but evolutionarily distant from VSV G protein. It thus appears that transmission of respiratory syncytial viruses lacking the attachment and fusion proteins can be achieved by including a diverse group of heterologous unrelated operating entry/exit proteins coupled to the respiratory syncytial virus F cytoplasmic tail domain. In general, any individual or combination of viral transmembrane glycoprotein(s) that provides attachment, entry and exit function can be used as replacement. Examples of these replacement proteins include, but are not limited to, the Filoviridae GP or the Flaviviridae E protein or combinations such as the F and H or HN transmembrane attachment and entry proteins of the Paramyxoviridae.

$G^{vsv}$ Efficiently Mediates Infectivity of an SH,G,F-Deleted Virus

The results presented demonstrate that all SH, G, and F functions necessary for infectivity and transmission of human respiratory syncytial virus in cell culture can be provided by a single heterologous transmembrane glycoprotein carrying the F protein cytoplasmic tail domain ($G^{vsv}$). Moreover, this functional substitution was efficient as engineered virus RSΔSH,G,F/$G^{vsv}$ was infectious to both Vero and HEp-2 cells and replicated in either cell type to wt level titers. In contrast, previous work showed that human respiratory syncytial viruses lacking the G gene replicated efficiently in Vero cells but were significantly growth-impaired in HEp-2 cells (Karron et al., 1997; Teng et al., 2001). Thus, by providing a foreign viral glycoprotein, one can expand the range of cell types in which G-deleted viruses can be propagated. The efficiency of substitution further suggests that beyond providing access to the cell cytoplasm, no additional G and F functions were required for initiation of infection or for production of infectious progeny virions in cell culture. A possible exception is the F protein cytoplasmic tail domain, as this domain was included in the chimeric protein used to replace SH, G, and F in virus RSΔSH,G,F/$G^{vsv}$.

HRSV can be Modified to Initiate Infection Via an Endosomal Entry Route

Because VSV and respiratory syncytial virus have different entry mechanisms (Dahlberg et al., 1974; Matlin et al., 1982; Srinivasakumar et al., 1991), the strategy of replacing SH, G, and F with a VSV G-derived membrane glycoprotein provided insight into the ability of respiratory syncytial virus to utilize an alternate entry pathway. Consistent with previous reports, the virus carrying wt respiratory syncytial virus G and F proteins (RSΔSH) was not affected by ammonium chloride, a compound known to block entry of VSV and other viruses that require an acidification step during entry (Marsh and Helenius, 1989). In contrast, infectivity of virus RSΔSH,G,F/$G^{vsv}$ was severely inhibited by ammonium chloride, showing utilization of an entry pathway that differed from wt respiratory syncytial virus. Because RSΔSH, G,F/$G^{vsv}$ infectivity was mediated by and dependent on $G^{vsv}$ and required an acidification step, this pathway most likely occurs through clathrin-coated vesicles similar to that of VSV virions (Doxsey et al., 1987; Marsh and Helenius, 1989). This suggests that, when provided with an appropriate receptor binding protein and the means to cross the endosomal membrane, the human respiratory syncytial virus ribonucleoprotein can productively initiate infection after release from endosomes.

Virus RSΔSH,G/$G^{vsv}$, which expresses two fusion-competent glycoproteins ($G^{vsv}$ and HRSV F), failed to initiate infection in Vero and HEp-2 cells in the presence of ammonium chloride. This was surprising because previous reports using a virus in which the human respiratory syncytial virus SH and G genes were deleted and not replaced, showed that F alone was able to mediate efficient propagation in Vero cells (Karron et al., 1997; Techaarpornkul et al., 2001). However, in these viruses the F gene was now in seventh position relative to the 3' end of the genome instead of its wild type eighth position, and its expression therefore was likely upregulated (due to the obligatorily sequential transcription with attenuation at each gene junction). The inability of F to mediate RSΔSH,G/$G^{vsv}$ entry in the presence of ammonium chloride was probably not due to ammonium chloride or to the F protein itself, as infectivity of virus RSΔSH was not affected by the same compound (FIG. 6B) and RSΔSH,G/$G^{vsv}$ infected cells formed pH-independent syncytia in the absence of ammonium chloride, indicating fusion competency. Thus, $G^{vsv}$ appeared to dictate the mode of entry and the HRSV F protein was unable to initiate infection in its presence.

It was previously reported that, in HEp-2 cells, the F protein was able to mediate pH-independent entry of a recombinant VSIV virus which retained its homologous G protein, in the presence of ammonium chloride (Kahn et al., 1998). Although the efficiency of this pH-independent entry process was not directly measured, it raises the possibility that differences exist between the human respiratory syncytial, virus and VSIV systems that may allow different degrees of F-mediated, pH-independent entry.

Infectivity Remains Predominantly Cell-Associated in the Absence of SH, G, and F Proteins Budded RS virions remain predominantly associated with the cell surface (Levine and Hamilton, 1969; Roberts et al., 1995; FIG. 7), and this is also true for Measles virus (MeV), a paramyxovirus from the genus *Morbillivirus*. In a similar study, genes encoding attachment protein H and fusion protein F were deleted from the measles genome and replaced with the VSIV G gene carrying the cytoplasmic tail domain of MeV F protein. Infectious viruses were recovered, but replication in Vero cells was substantially delayed and viral titers were reduced 10- to 50-fold (Spielhofer et al., 1997). Notably however, this engineered MeV was now efficiently released to the supernatant of infected cells, instead of being predominantly cell-associated. In contrast, replacement of the human respiratory syncytial virus SH, G, and F open reading frames with that of $G^{vsv}$ did not increase the proportion of infectious RS virions in the supernatant of infected Vero cells, nor did it significantly delay or lower viral yields (FIG. 7). These results indicate significant differences between human respiratory syncytial virus and MeV in the requirements of homologous glycoproteins to drive efficient cell-to-cell transmission, and in the mechanisms by which HRSV and MeV remain associated to the cell surface.

Virus-Induced Filaments Form at the Surface of Engineered and A2 Virus-Infected Cells Filamentous structures are formed at the cell surface after infection of various cell types, both polarized and unpolarized, with human respiratory syncytial virus (Fuchs and Bächi, 1975; Faulkner et al., 1976; Parry et al., 1979; Bächi, 1988; Roberts et al., 1995). These filaments are sites where the G and F proteins concentrate and vary significantly in length and appearance, ranging from single discrete filaments of 0.1 µm diameter and between 1 and 10 µm in length, to bundles of filaments of various length often observed as dense clusters. This morphology does not appear to be a consequence of tissue culture adaptation. A predominant filamentous nature was also observed in cells infected with human respiratory syncytial virus directly isolated from patients, and in autopsy material (Joncas et al., 1969; Bryson et al., 1991).

In cells infected with the engineered human respiratory syncytial viruses generated here, it was observed that filamentous structures similar to those previously described for a wt human respiratory syncytial virus formed in abundance at the cell surface even when all three transmembrane glycoproteins were replaced by a single foreign viral glycoprotein carrying the F cytoplasmic tail domain. Thus, although the virus-induced filaments appear to be sites where the glycoproteins concentrate, the SH and G proteins, as well as the F protein ecto and transmembrane domains are not essential for the formation or maintenance of these structures.

These results appear consistent with previous findings in VSIV and Rabies virus, where M protein was the predominant determinant of particle morphology (Lyles et al., 1996; Mebatsion et al., 1998). In contrast to VSIV, for SV5 (another member of the Paramyxoviridae), coexpression of the nucleocapsid protein, the M protein, and one of the homologous glycoproteins was required for efficient particle assembly (Schmitt et al., 2002). It is not known whether interactions between the M and F proteins are important for the human respiratory syncytial virus assembly process. HRSV M was shown to have independent membrane binding ability, and in contrast to MV and Sendai virus, the human respiratory, syncytial virus M and F proteins did not co-localize in the cytoplasm of infected cells (Henderson et al., 2002). However, the M and F protein co-localized at the plasma membrane and the F protein had an effect on the degree to which M associated with lipid rafts. Together these findings suggest that the human respiratory syncytial virus matrix protein may be a central organizer of the assembly process, and that interactions between M and the glycoproteins may play a role. Whether the F protein cytoplasmic tail domain is required for efficient incorporation of glycoproteins into virus particles or whether the F protein cytoplasmic tail domain and M protein are essential components of the observed filamentous structures remains to be established.

Alternatives and Improvement to Current Vaccine Development Strategies

Results disclosed herein show that a heterologous membrane glycoprotein could functionally and efficiently replace the respiratory syncytial virus membrane glycoproteins. The results of the present strategy open a way to develop a system to further examine the roles of individual or combinations of respiratory syncytial virus glycoproteins in respiratory syncytial virus biology and pathogenesis. Combined with the development of tissue culture systems that approach in vivo conditions, such as well-differentiated human airway epithelial cells, this would expand our understanding of the role of the SH, G, and F glycoproteins in the respiratory syncytial virus life cycle and improve the ability to use engineered respiratory syncytial viruses for vaccine purposes or other medical applications.

The new approach described herein offers improvements to several of the drawbacks of the current vaccine candidates. The basis of the improvements lies in constructing recombinant respiratory syncytial viruses that completely lack the G, F, and SH proteins by incorporating in the genome a heterologous single entry protein. This strategy frees us from the constraints of needing the G and F proteins to make infectious virus, and allows one to add back one at a time whole or segments of various respiratory syncytial (or other) genes to assess their roles in pathogenesis or immunity (i.e. what is needed to constitute a vaccine—both cell mediated and humoral immunity).

Alternatively, the heterologous entry protein can be provided by complementation to make a pseudotype without incorporating the gene into the virus genome. This pseudotype virus would be self-limited. Nevertheless, in spite of the absence of all respiratory syncytial virus envelope glycoproteins, and unlike the current cp52-based candidate, high titers of these recombinant viruses can be generated in a variety of cell lines. High titers and complete absence of all major native glycoproteins combined with the positions in the genome now available allow one to construct by design the genes one wishes to express from the genome. This allows for the inclusion of homologous or heterologous genes of choice or selected subsets chosen from the homologous genes.

The above findings, in particular the novel fact that relatively high titers of respiratory syncytial virus can be grown in the complete absence SH, G, and F proteins, provides several alternatives and potential improvements to the current vaccine strategies. In particular it provides advantages for determining how to construct a vaccine that is both safe and efficacious and a method to construct the indicated vaccine. These advantages include:

I) Strict Control Over Respiratory Syncytial Virus Envelope Glycoprotein Components Uncompromised independence from all major envelope respiratory syncytial virus envelope glycoproteins (SH, G, and F) allows testing of these structural components for safety and immunogenicity in the background of a live, transmissable virus. Minimal epitopes eliciting a protective, appropriate immune response can thus be systematically mapped, segregated from those evoking harmful immune reactions, and selectively included in a vaccine candidate lacking complete and functional SH, G, or F, produced in the presence of a heterologous entry protein. Therefore, one could put back entire individual RSV gene or parts of the gene to determine which parts of each RSV protein contain protective epitopes and which regions contain potentially pathogenic enhancing or detrimental epitopes.

II) Improved Control Over Transmission Competency

Acquiring a level of viral transmission that allows for a safe yet effective respiratory syncytial virus vaccine has been a major challenge. The system disclosed herein is the first to make it possible to generate an infectious, replicating yet non-transmitting respiratory syncytial virus by providing a heterologous entry protein in trans to an engineered respiratory syncytial virus completely lacking SH, G, and F proteins. This is aided by the fact that respiratory syncytial virus and the recombinant virus disclosed herein, unlike VSV for example, do not efficiently shut down the host cell metabolism, thus allowing continued availability of a heterologous protein provided in trans during production of a vaccine candidate. As an added benefit, the absence of SH, G, and F proteins in the recombinant respiratory syncytial viruses disclosed herein provides selective pressure to include the protein provided in trans, thereby further aiding the generation of sufficiently high titers. Cell lines expressing functional VSV-G have been previously generated, and cell lines expressing Baculo GP64 was generated in the present invention.

Due to the presence of trans-provided envelope protein, efficient entry, replication and expression of desired safe and antigenic epitopes should be far superior in evoking an immune response over killed, inactivated vaccines. Respiratory syncytial viruses expressing no SH, G, and F entry proteins will possess the same advantages as killed, inactivated vaccines do, i.e. abolish transmission and reduced risk of reversion to more aggressive phenotypes, problems common to all live vaccines currently being considered. It will have the benefit of stimulating cell mediated responses which only live attenuated vaccines do. If non-transmission elicits insufficient immune response, a replicating non-transmitting virus will be an excellent starting point to fine-tune a desired level of transmission by including combinations of selected wild type or mutant heterologous or homologous entry proteins.

III) Improved Control Over the Target Tissue and Type of Immune Response Generated Envelope glycoproteins are generally important factors in directing a virus to its target location. Presence of all or a subset of the major envelope glycoproteins in the current respiratory syncytial virus vaccine candidates directs targeting of such candidates to the URT and LRT, and as such may narrow the type of immune response to be expected from a vaccinated individual. In the present invention, since all major respiratory syncytial virus glycoproteins can be selectively deleted and specific targeting proteins can be inserted in the available spaces within the respiratory syncytial virus virus genome, the location to which the vaccine candidate is targeted can be manipulated. Consequently, one can control with more accuracy how a vaccine is presented to the immune system and what type of immune response is generated. Examples of targeting proteins are RSV G protein with epitopes implicated in causing enhanced pathogenesis being deleted; an F protein with any epitopes that might be identified as being involved in enhanced disease being omitted; epitopes or entire genes from other viruses such as the HPIV I or III F or HN proteins, or influenza HA or NA proteins. These mentioned genes variously have the ability to target the viruses apically, or basolaterally, or to respiratory or other tissues as desired.

IV) Enhanced Stability/Solubility of RS Virions

Particularly for respiratory syncytial virus, the demonstrated unstable nature of the virion remains a significant problem in producing a sufficiently stable vaccine. Both VSV G and GP64 are the major envelope glycoprotein of a naturally soluble, stable virion. The presence of VSV G for example has been shown to have a stabilizing effect when included in the envelopes of retrovirions. Also, the fact that two such diverse membrane glycoproteins (from VSV, a rhabdovirus and AcMNPV, a baculovirus) are capable of directing respiratory syncytial virus transmission might be exploited to enhance in vivo half-life of an introduced live or inactivated virus. Vaccinations with recombinant respiratory syncytial viruses alternatingly displaying ectodomains of VSV G, baculovirus GP64 or other yet undefined entry proteins may help prevent premature clearance of the administered virus by the immune system.

Potential for Use in Drug Discovery/Screening

Furthermore, recombinant respiratory syncytial viruses disclosed herein are excellent candidate viruses to use in methods of screening for antiviral agents. Comparing the effects of antiviral agents on the recombinant respiratory syncytial viruses disclosed herein with those on the wild type respiratory syncytial viruses one can distinguish between inhibitors that affect intracellular replication events from inhibitors that affect the attachment, infectivity or spread of respiratory syncytial viruses.

In accordance with the present invention; there may be employed conventional molecular biology, microbiology, and recombinant DNA techniques within the skill of the art. Such techniques are explained fully in the literature. See, e.g., Maniatis, Fritsch & Sambrook, "Molecular Cloning: A Laboratory Manual (1982); "DNA Cloning: A Practical Approach," Volumes I and II (D. N. Glover ed. 1985); "Oligonucleotide Synthesis" (M. J. Gait ed. 1984); "Nucleic Acid Hybridization" [B. D. Hames & S. J. Higgins eds. (1985)]; "Transcription and Translation" [B. D. Hames & S. J. Higgins eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984). Therefore, if appearing herein, the following terms shall have the definitions set out below.

As used herein, the term "antiviral compound" refers to any substance which inhibits the replication of a virus or inhibits any essential process in the replication cycle.

As used herein, the term "negative strand RNA virus" is defined as a classification of RNA viruses in which the genome comprises the negative strand of an RNA molecule.

As used herein, the term "heterologous entry protein" is defined as a protein or proteins providing attachment and entry as well as assembly, maturation and exit functions.

In one embodiment of the present invention, there is provided a recombinant respiratory syncytial virus (RSV) in which all of the surface glycoprotein genes encoding the attachment protein G, the fusion protein F, and the Small Hydrophobic protein SH are deleted and replaced by a gene encoding a heterologous protein that mediates cell infection and entry activity of said respiratory syncytial virus. The replacement heterologous protein can be derived, for example, from the G protein of Vesicular Stomatitis Virus or the GP64 protein of baculovirus fused to the cytoplasmic tail domain of respiratory syncytial virus F protein. Alternatively, the replacement heterologous protein is not fused to the cytoplasmic tail domain. Furthermore, at least one marker gene encoding β-glucuronidase or green fluorescent protein may also be incorporated into the recombinant respiratory syncytial virus.

In another embodiment of the present invention, there is provided a method of making a recombinant respiratory syncytial virus (RSV) that can infect a cell but cannot spread beyond the cell. Firstly, a recombinant respiratory syncytial virus is constructed in which the genes encoding the attachment protein G, the fusion protein F, and the Small Hydrophobic protein SH are deleted. Then a heterologous protein that mediates cell infection of the respiratory syncytial virus is provided in trans, thereby generating a respiratory syncytial virus that can infect a cell but cannot spread beyond said cell. Representative heterologous proteins are described above and those that can be provided in trans include but are not limited to the G protein of Vesicular Stomatitis Virus and the GP64 protein of baculovirus.

In yet another embodiment of the present invention, there is provided a method of targeting a recombinant respiratory syncytial virus. The method involves deleting genes encoding the attachment protein G, the fusion protein F, and the Small Hydrophobic protein SH from a respiratory syncytial virus. The deleted genes are then replaced with a gene encoding a heterologous protein that mediates cell infection, entry, assembly, maturation and targeting of the respiratory syncytial virus. In one embodiment, the replacement gene encodes a chimeric protein comprising the heterologous protein and the G or F protein of a respiratory syncytial virus. Virtually any individual or combination of transmembrane proteins providing attachment/entry function could be used as the replacement heterologous protein. These proteins could be selected from proteins involved in recognition of a given virus or microbial pathogen. Representative heterologous proteins that mediate cell infection and targeting include, but are not limited to, the F protein of HPV I, F protein of HPV III, HN protein of HPV I, HN protein of HPV III, HA protein of influenza, NA protein of influenza, Ebola GP protein, Flavivirus E protein, Nipah virus F protein, Hendra virus F proteins, Measles virus F protein and Measles virus H protein.

In another embodiment of the present invention, there is provided a method of testing immunogenicity of an epitope of the surface glycoprotein of respiratory syncytial virus in a background of a live and transmissible virus. A gene encoding the epitope is incorporated into a respiratory syncytial virus in which all of the surface glycoprotein genes encoding the attachment protein G, the fusion protein F, and the Small Hydrophobic protein SH are deleted. The resulting recombinant respiratory syncytial virus allows testing of the epitope in a background of a live and transmissible virus.

The following examples are given for the purpose of illustrating various embodiments of the invention and are not meant to limit the present invention in any fashion.

EXAMPLE 1

Cells And Antibodies

Two cell types acquired from American Type Culture Collection (ATCC) were used: HEp-2 and Vero 76 cells. The A2 strain of RS virus was used as a comparison to the engineered viruses. Infections were carried out in standard growth media containing 5% FBS for 1.5 h at 37° C.

Monoclonal antibodies Mab 19 and Mab 6 were kindly provided by Geraldine Taylor, and MAb L9 by Ed Walsh. The humanized anti-F MAb Synagis was acquired from MedImmune, Inc. The anti-VSIV G Indiana and anti-Vesicular stomatitis New Jersey virus (VSNJV) antibodies were mouse ascitic fluids acquired from ATCC.

EXAMPLE 2

Construction of Chimeric Protein $G^{vsv}$

Figures 1A, 1B:
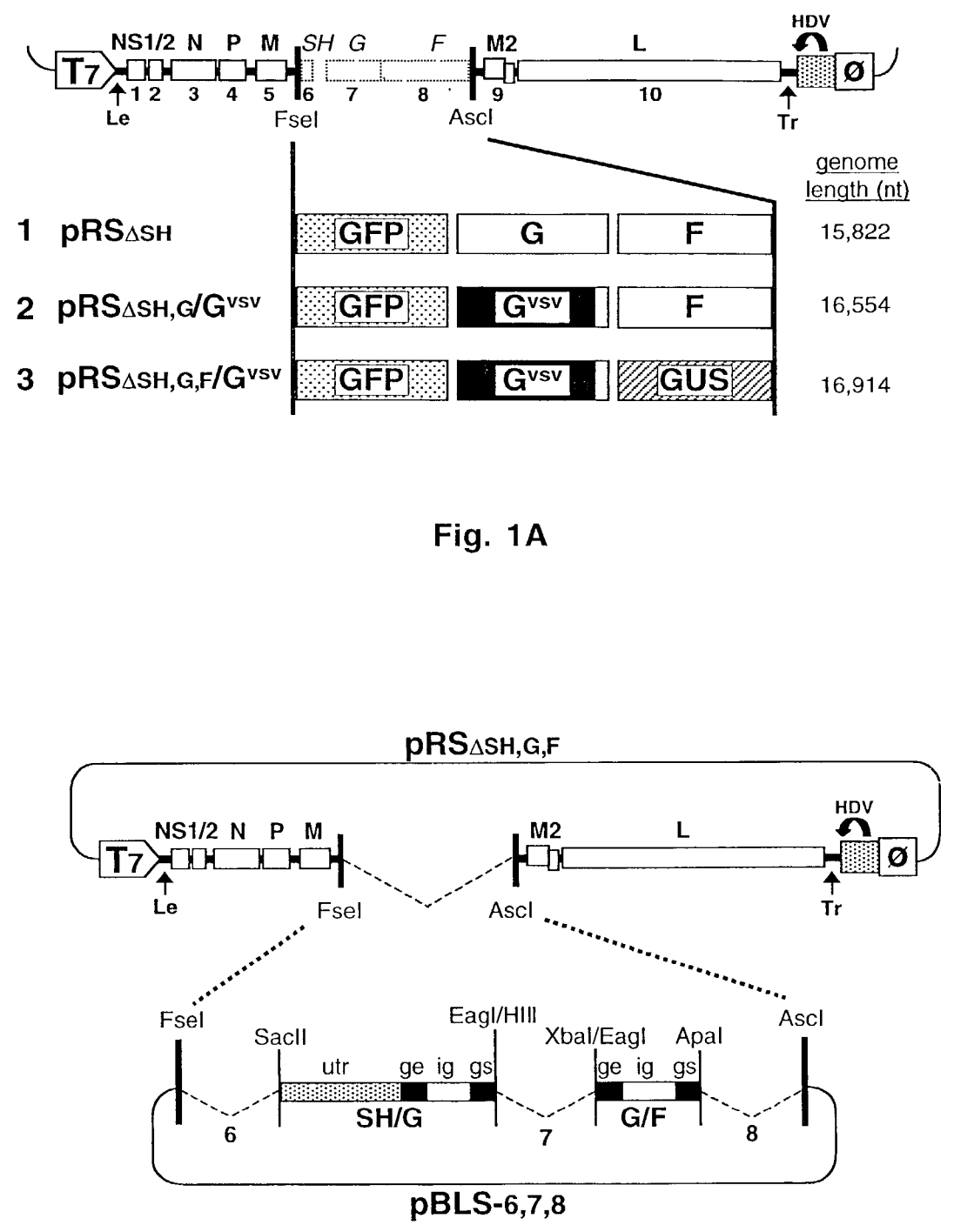

A truncated VSIV G Indiana ORF (amino acid 1 to 491) flanked by a 3' XbaI restriction site was generated using PCR. Nucleotides encoding amino acids 553 to 574 of human respiratory syncytial virus F protein (the cytoplasmic tail domain as predicted by hydrophobicity profiles, MacVector 7.0, Oxford Molecular) were amplified using PCR creating an XbaI site that overlapped amino acid 553. The engineered XbaI site was used to ligate the two fragments resulting in a chimeric protein, $G^{vsv}$ (see FIG. 1C).

EXAMPLE 3

Construction of Viral cDNAs, and Recovery of Engineered Human Respiratory Syncytial Virus with Altered Glycoprotein Gene Content A cDNA of the prototype A2 strain of human respiratory syncytial virus (HRSV) was generated by RT-PCR of HRSV RNAs and cloned into plasmid pBluescript (Stratagene) using convential cloning techniques. A T7 promotor followed by three guanosine residues to enhance transcription and a T7 terminator preceded by the hepatitis delta virus (HDV) ribozyme sequence were cloned on either side of the cDNA. Consequently, in the presence of the T7 polymerase, a (+) sense RNA is transcribed. From this transcript, viral genomic RNAs with precise 3' and 5' ends can be replicated by the viral polymerase, initiating an authentic viral infection (Pattnaik et al., 1992; Conzelmann and Schnell, 1994; Whelan et al., 1995).

Using conventional cloning techniques, the above described cDNA-containing plasmid was modified by deleting the area from the translation initiation codon of SH to the translation termination codon of F, and inserting unique restriction sites (FseI and AscI) in its place (pRSΔSH,G,F, see FIG. 1B). A second plasmid vector named pSH/G/F was constructed, containing the exact HRSV genomic region deleted in pRSΔSH,G,F, and also flanked by FseI and AscI restriction sites. The three open reading frames contained within pSH/G/F were removed and each replaced with a linker containing unique restriction sites, creating construct pBLS-6,7,8 (see FIG. 1B). pBLS-6,7,8 thus contained intergenic regions, transcription signals, and 3' and 5' untranslated regions that were unaltered from those of virus A2. The indicated glycoprotein and/or marker open reading frames were cloned into pBLS-6,7,8, and the resulting shuttle vectors were inserted in the pRSΔSH,G,F backbone via the FseI and AscI sites to generate the final cDNA containing plasmids (see FIG. 1A).

pRSΔSH,G,F was used to engineer cDNAs with an altered glycoprotein gene content. cDNAs that lacked one, two, or all three of the HRSV transmembrane glycoprotein open reading frames were generated. Each deleted open reading frame was replaced as follows: the SH open reading frame was replaced with that of GFP; the F open reading frame was replaced with that of marker protein GUS; and the G open reading frame was replaced with that of $G^{vsv}$, a chimeric glycoprotein based on the VSIV G protein. VSIV G contains attachment, fusion, and assembly/exit functions within a single protein, and has been successfully used to enhance infectivity of other distantly related viruses (Marsh and Helenius, 1989; Emi et al., 1991; Burns et al., 1993). However, because the cytoplasmic tail domain of viral glycoproteins can play a critical role in glycoprotein incorporation and virion budding and morphology, the VSIV G open reading frame was modified by exchanging the sequence encoding its predicted cytoplasmic tail domain (amino acids 492–512) with that of human respiratory syncytial virus F (amino acids 553 to 574) (FIG. 1C) (Mebatsion et al., 1996; Jin et al., 1997; Schnell et al., 1998; Takimoto et al., 1998; Oomens et al., 1999; Schmitt et al., 2002). The product of this chimeric open reading frame was termed $G^{vsv}$.

Three cDNAs were constructed (FIG. 1A) that varied only in the content of open reading frames in genome positions six, seven and eight. pRSΔSH contains the homologous human respiratory syncytial virus G and F open reading frames preceded by that of GFP. pRSΔSH,G/$G^{vsv}$ lacks the SH and G open reading frames and contains instead those of GFP and $G^{vsv}$. pRSΔSH,G,F/$G^{vsv}$ lacks all three homologous transmembrane glycoprotein open reading frames, SH, G, and F, and contains instead those of GFP, $G^{vsv}$, and GUS. Infectious viruses were recovered from all cDNAs, and designated RSΔSH, RSΔSH,G/$G^{vsv}$, and RSΔSH,G,F/$G^{vsv}$ respectively.

Virus Recovery

Viruses were recovered from the cDNA as follows. HEp-2 cells (0.5×10⁶ cells per well) infected with modified Vaccinia Ankara-T7 virus (Wyatt et al., 1995) at a multiplicity of 5 for 1.5 hours were transfected with plasmids containing a modified human respiratory syncytial virus cDNA and plasmids encoding each of the proteins required for transcription and replication of viral RNA (N, P, L, and M2-1) using Lipofectin (Invitrogen) (Hardy et al., 1999). For each transfection, 0.1 µg of cDNA plasmid was used, along with approximately 0.35, 0.2, 0.25, and 0.05 µg respectively of plasmids encoding the N, P, M2-1, and L proteins. Cells were incubated at 37° C. for 70 hours, at which time supernatants were collected and added to fresh Vero cells. After 24 hours at 33° C., the supernatant was replaced with fresh medium, and cells were incubated for another 7 days at 33° C. Virus was collected from the supernatants, amplified on Vero cells, and stocks generated and stored at -80° C. (approximately 10⁷ PFU/ml). The RNAs of engineered virus stocks between passage 4 and 6 were verified by RT-PCR and sequence analysis across cloning junctions and in modified areas.

Titration of Virus Stocks

Virus was adsorbed to cells for 1.5 hours at 37° C., then overlayed with 0.5% agar. At 5 days postinfection, 4% formaldehyde in PBS was added to the overlay, and incubated for 30 min at room temperature. Agar was removed and cells fixed for an additional 5 min in methanol. The protocol for visualization of antigens was an adaptation of an existing β-galactosidase detection assay (Sussman, 1995). Fixed cells were incubated with either anti-VSIV G antibodies (for viruses RSΔSH,G/$G^{vsv}$ and RSΔSH,G,F/$G^{vsv}$) or anti-F antibodies (for viruses RSΔSH and virus A2), followed by incubation with a β-galactosidase conjugated goat-anti-mouse antibody (Southern Biotechnology Associates, Inc). After washing with PBS, cells were incubated overnight at 20° C. in a solution of 0.5 mM potassium ferricyanide/0.5 mM potassium ferrocyanide/0.1 mM MgSO₄/0.15 mg/ml X-gal in PBS. Samples were washed twice with H₂O, dried, and plaques counted.

EXAMPLE 4 mRNA Expression by the Engineered Viruses

The expression of mRNAs by the engineered human respiratory syncytial viruses was compared to that of virus A2. Vero cells infected at a multiplicity of 2 were exposed to ³H-uridine in the presence of 10 µg/ml actinomycin D, for 16 to 22 hours. Total RNA was isolated using RNeasy columns (Qiagen), and 3' poly(A) tails were removed by annealing with oligo(dT) followed by digestion with RNase H (Hardy et al., 1999). RNAs were electrophoresed on 1.75% agarose gels containing 6 M urea and 25 mM citrate, and visualized by fluorography.

The profiles of labeled mRNAs are shown in FIG. 2. The positions of monocistronic A2 mRNAs are indicated on the left (Collins and Wertz, 1983; Collins et al., 1984). The engineered viral genomes all lacked the open reading frame of the SH gene and hence did not express the SH mRNA; instead, they expressed an mRNA consistent with the size of the GFP open reading frame inserted in its place (FIG. 2, compare lanes 1 and 2–4). Virus RSΔSH,G/$G^{vsv}$ did not express either the SH or G mRNAs (FIG. 2, lane 3), and virus RSΔSH,G,F/$G^{vsv}$ expressed neither SH, G or F mRNAs (FIG. 2, lane 2). Instead, these viruses expressed the $G^{vsv}$ mRNA (FIG. 2, lanes 2 and 3), and additionally, in the case of RSΔSH,G,F/$G^{vsv}$, an mRNA corresponding to the predicted size of the inserted GUS open reading frame was expressed (FIG. 2, lane 2). In each case, the appropriate mRNA for the deleted open reading frame was missing and in its place the appropriate mRNA for the inserted open reading frame was expressed.

EXAMPLE 5

Protein Expression by the Engineered Viruses

Transmembrane glycoprotein expression by each of the viruses was examined by immunofluorescence. Vero cells infected at a multiplicity of 2 were fixed at 16 hours (for G protein) or 24 hours (for proteins $G^{vsv}$ and F) postinfection with methanol at 20° C. or freshly dissolved 4% paraformaldehyde for confocal microscopy. Fixed cells were washed and blocked, then incubated with anti-F; anti-G, or anti-VSIV G antibodies. The cells were then incubated with either a goat-anti-mouse or rabbit-anti-human antibody carrying a fluorescent conjugate (alexa-594 or alexa-350; Molecular Probes). For confocal microscopy, nuclei of A2 infected cells were visualized with Hoechst stain. Cells were photographed on a Zeiss Axioscope microscope or scanned on a Leica TCS NT confocal microscope system for dual detection of GFP and viral antigens.

Figure 3:
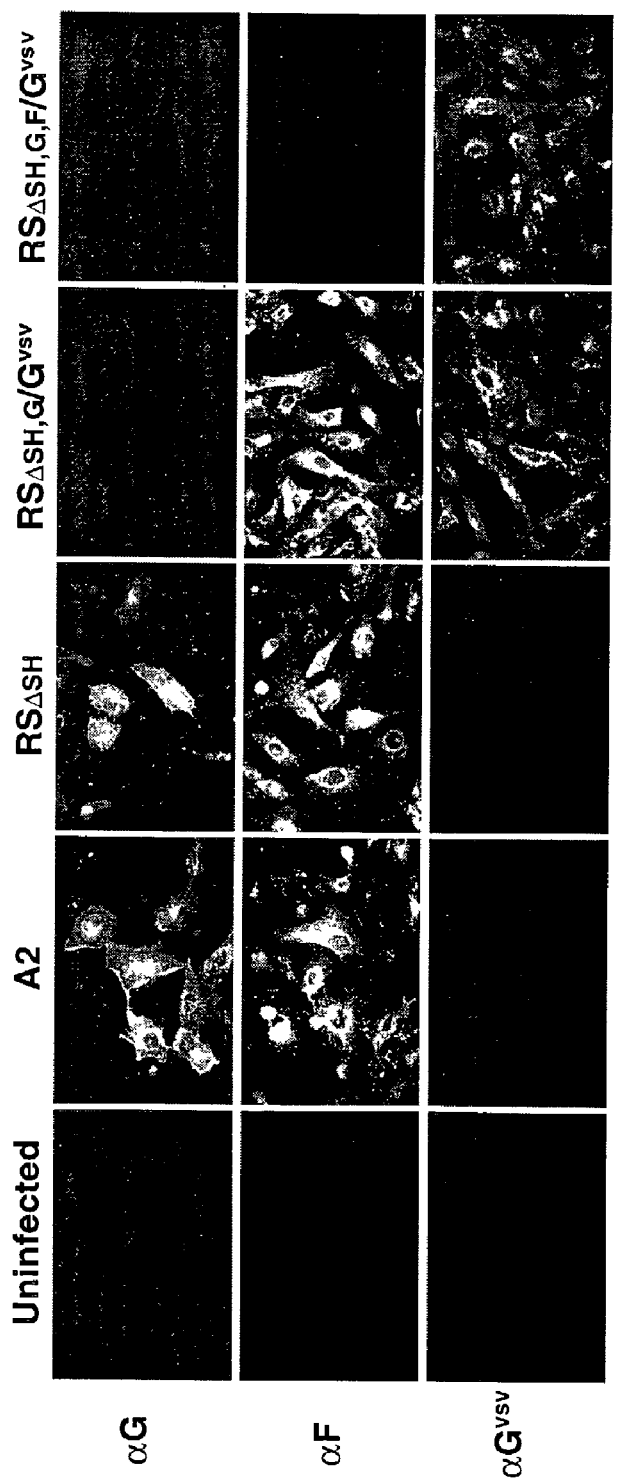
FIG. 3 shows transmembrane glycoprotein expression by the engineered viruses. Vero cells infected with each of the engineered viruses and virus A2 were fixed with methanol and incubated with antibody L9 directed against the human respiratory syncytial virus G protein (anti-G), antibody MAb19 directed against the human respiratory syncytial virus F protein (anti-F), or an anti-VSV G Indiana antibody (anti-VSV G). After incubation with a secondary antibody carrying an alexa-594 fluorescent conjugate, samples were examined on a fluorescent microscope and photographed (magnification 400×). Uninfected Vero cells were included as a control.

As shown in FIG. 3, neither the human respiratory syncytial virus G nor F proteins were detected in cells infected with virus RSΔSH,G,F/$G^{vsv}$; instead the $G_{vsv}$ protein was detected. Engineered virus RSΔSH,G/$G^{vsv}$ also lacked expression of the HRSV G protein, but expressed both $G^{vsv}$ and the HRSV F protein. In cells infected with viruses RSΔSH and A2, which carry wt human respiratory syncytial virus G and F genes and no heterologous glycoprotein ORFs, both human respiratory syncytial virus G and F proteins were expressed, but not $G^{vsv}$. These results were in agreement with the genome content of each of the viruses, and confirmed that in engineered virus RSΔSH,G,F/$G^{vsv}$, the only transmembrane glycoprotein expressed was chimeric protein $G^{vsv}$.

EXAMPLE 6

Analysis of $G^{vsv}$ Function

During entry of VSIV virions via endocytosis, the acidification of endosomes triggers the VSIV G protein to induce virus-cell membrane fusion which allows entry of the nucleocapsid into the cytoplasm. This capacity to induce membrane fusion can be demonstrated by exposing cells that express VSIV G at the cell surface to low pH medium, which leads to fusion between adjacent plasma membranes and formation of multi-nucleated syncytia (Florkiewicz and Rose, 1984; Marsh and Helenius, 1989). To examine the membrane fusion capacity of chimeric protein $G^{vsv}$, syncytium formation assay was carried out as follows. Vero cells were infected with viruses RSΔSH,G,F/$G^{vsv}$ and RSΔSH,G/$G_{vsv}$, or RSΔSH as a control, at a multiplicity of 1. Infection was allowed to proceed for 20 hours, at which time the cells were exposed to PBS at pH 5.0 or pH 7.0 for 3 minutes. Cells were then incubated in normal growth medium for one hour, fixed with 4% paraformaldehyde, and photographed on a Zeiss Axiovert microscope using phase contrast or UV light for GFP visualization.

Figure 4:
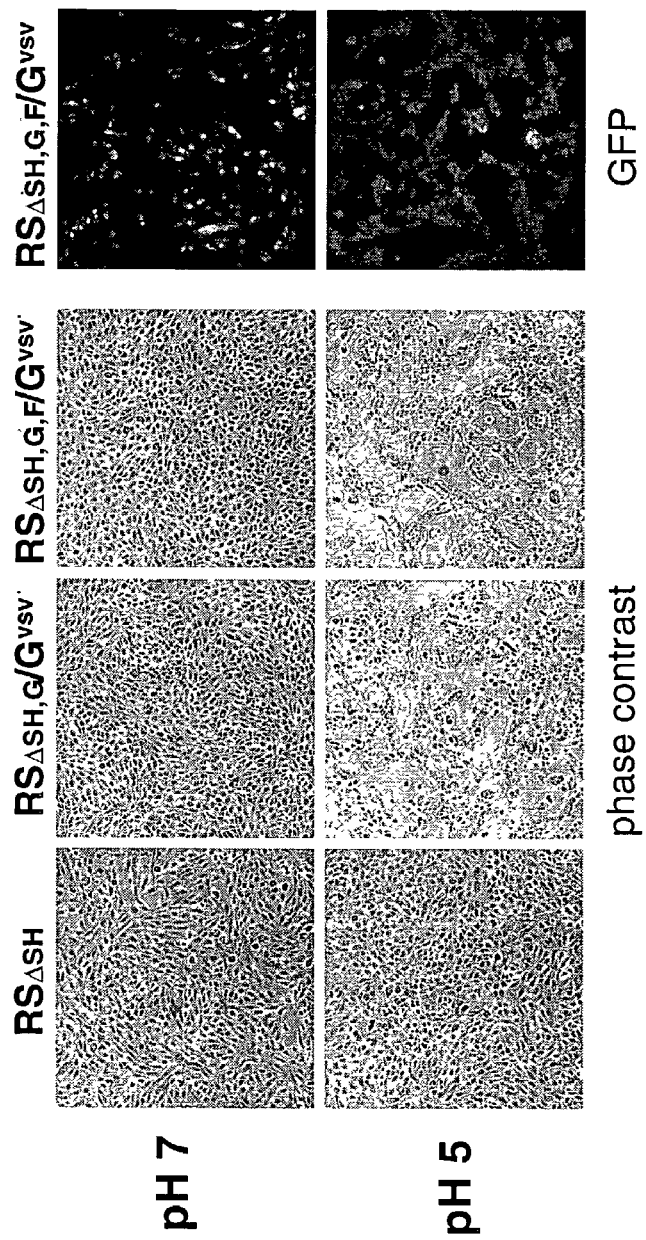
FIG. 4 analyzes $G^{vsv}$ fusion capacity by cell-cell membrane fusion assay. Vero cells infected with viruses RSΔSH, G/$G^{vsv}$, RSΔSH,G,F/$G^{vsv}$, or RSΔSH, were exposed for 3 min to pH 7 (top panels) or pH 5 medium (bottom panels) at 20 hours postinfection. Cells were further incubated in normal growth medium for 1 hour, fixed with 4% paraformaldehyde, and photographed (phase contrast; magnification ~100×). RSΔSH,G,F/$G^{vsv}$ infected cells were also photographed on a fluorescence microscope (GFP).

Extensive cell-cell membrane fusion and formation of multi-nucleated syncytia was observed in RSΔSH,G,F/$G^{vsv}$ and RSΔSH,G/$G^{vsv}$ infected cells after treatment at pH 5.0 (FIG. 4, lower panels) but not at pH 7.0 (FIG. 4, upper panels). This indicated that chimeric protein $G^{vsv}$ migrated to the cell surface and was fusion-activated by low pH. As expected, low-pH induced syncytia were not formed in RSΔSH infected cells. However at later times postinfection, multi-nucleated syncytia appeared gradually in RSΔSH infected cells in a pH-independent manner, as typically observed with wt HRSV (data not shown).

EXAMPLE 7

Infectivity of RSΔSH,G,F/$G^{vsv}$ is Neutralized by $G^{vsv}$ Specific Antibodies To determine whether infectivity of RSΔSH,G,F/$G_{vsv}$ virions was mediated by $G^{vsv}$, the effect of anti-VSIV G specific (anti-$G^{IN}$) antibodies on the infectivity of RSΔSH,G,F/$G^{vsv}$ to Vero cells was examined. As a control, antibodies against Vesicular stomatitis New Jersey virus (VSNJV) (anti-$G^{NJ}$) were included. The anti-$G^{IN}$ and -$G^{NJ}$ antibodies neutralized their corresponding G proteins at similar concentrations. RSΔSH,G,F/$G^{vsv}$ virions (5×10⁴ PFU) was incubated in 250 μl normal cell growth medium+10 mM HEPES for 1 hour at room temperature in the presence of anti-VSIV G or anti-VSNJV antibodies at a range of dilutions. Vero cells were incubated with the pretreated virus for 1.5 hours at 37° C., after which the cells were washed 2× and incubated in normal growth medium at 37° C. At 28 hours postinfection, the cells were fixed with 4% paraformaldehyde, and photographed on a Leica TCS NT confocal microscope (FIG. 5).

Figure 5:
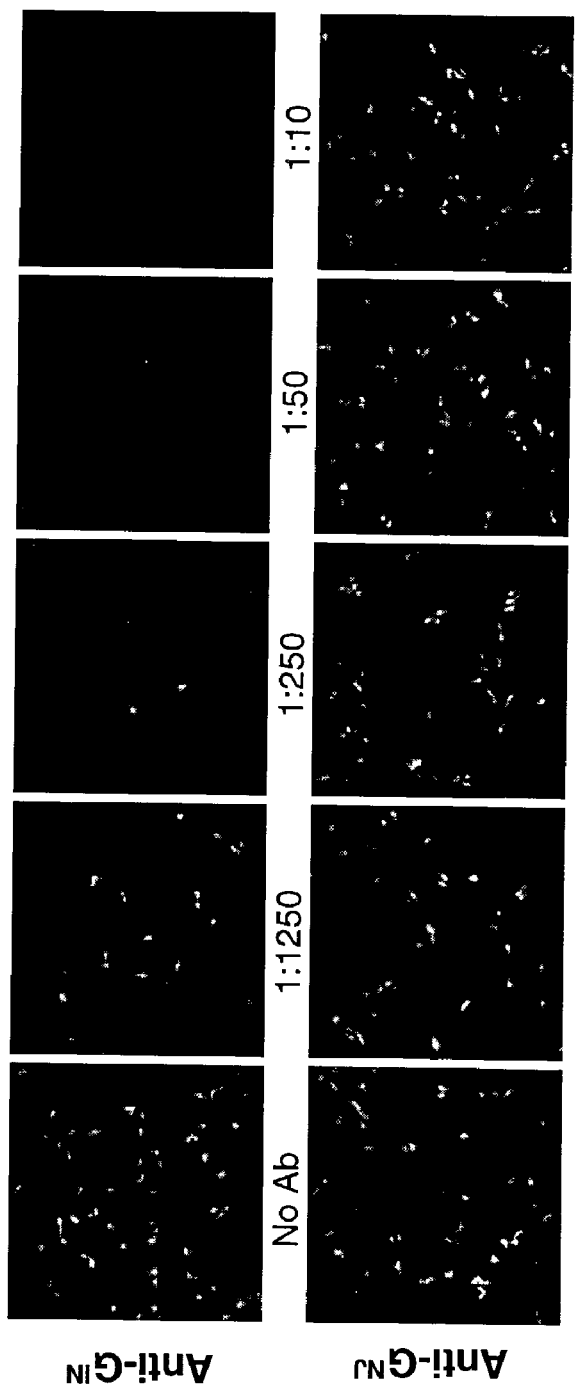
FIG. 5 shows the neutralization of RSΔSH,G,F/$G^{vsv}$ infectivity by anti-VSIV G antibodies. Virus RSΔSH,G,F/$G^{vsv}$ was pre-incubated with anti-VSIV G (anti-$G^{IN}$) or anti-VSNJV G (anti-$G^{NJ}$) antibodies in a range of dilutions. Pre-incubated virus was used to infect Vero cells for 1.5 hours, then removed by wash steps. At 20 hours postinfection, cells were fixed, examined by fluorescence miscroscopy (magnification ~100×). Concentrations of antibodies used are indicated.

Anti-$G^{IN}$ antibodies neutralized infectivity in a concentration-dependent manner (FIG. 5, upper panels). In contrast, even the highest concentrations of anti-$G^{NJ}$ antibodies had no effect on RSΔSH,G,F/$G^{vsv}$ infectivity (FIG. 5, lower panels). To test whether the neutralizing effect could have been due to secondary effects on HRSV or marker proteins expressed by RSΔSH,G,F/$G^{vsv}$, the anti-$G^{IN}$ antibodies were also used to treat the RSΔSH virus. Pre-incubated RSΔSH virus was unaffected in its ability to infect Vero cells even at the highest antibody concentrations (data not shown).

Together, this indicated that infectivity of virus RSΔSH,G,F/$G^{vsv}$ was mediated by the $G^{vsv}$ protein.

EXAMPLE 8

Virus RSΔSH,F/$G^{vsv}$ Utilizes an Altered, $G^{vsv}$-Dependent, Entry Mechanism VSIV virions enter via endocytosis, in which acidification of endosomes triggers the VSIV G protein to induce virus-cell membrane fusion, an event required for entry of the nucleocapsid. The endocytic entry pathway of VSIV virions can be blocked with compounds such as ammonium chloride that buffer the endosomal pH and thus prevent the acidification that induces virus-cell membrane fusion (Matlin et al., 1982; Helenius et al., 1982). In contrast to VSIV, human respiratory syncytial virus is believed to enter at the plasma membrane in a pH-independent manner, and it was shown previously that entry and replication of a wt human respiratory syncytial virus were not affected by ammonium chloride (Srinivasakumar et al., 1991).

To examine whether entry of virus RSΔSH,G,F/$G^{vsv}$ was sensitive to ammonium chloride, Vero cells were infected in the presence of a range of ammonium chloride concentrations. Vero cells were infected at a multiplicity of 0.5. Thirty minutes prior to virus adsorption, ammonium chloride was added to growth medium containing 25 mM HEPES. Concentrations of ammonium chloride were maintained during virus adsorption and postinfection incubation. At 24 hours postinfection, cells were fixed with 4% paraformaldehyde, mounted, and photographed on a Leica TCS NT confocal microscope.

Figure 6A:
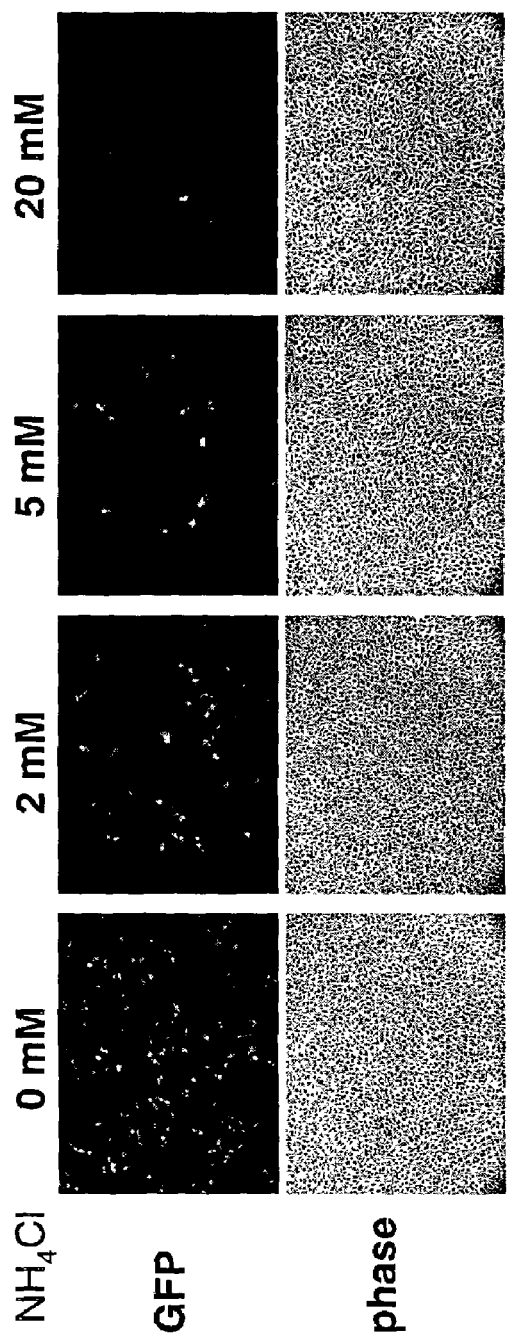
FIG. 6A shows the effect of ammonium chloride (NH$_4$Cl) on virus entry. Vero cells were infected with virus RSΔSH, G,F/$G^{vsv}$ for 1.5 hours at 37° C. in the presence of 0, 2, 5, or 20 mM NH$_4$Cl. Cells were then further incubated in presence of the same NH$_4$Cl concentrations. At 20 hours postinfection, cells were fixed with 4% paraformaldehyde and photographed with phase contrast (phase) or in the presence of UV light (GFP) (magnification ~60×).

Increasing amounts of ammonium chloride progressively inhibited RSΔSH,G,F/$G^{vsv}$ infectivity (FIG. 6A, upper panels) as measured by the number of cells expressing GFP, while cell viability was unaffected (FIG. 6A, lower panels). A concentration of 20 mM ammonium chloride led to nearly complete inhibition of infectivity, as has been shown for other viruses that utilize this pathway (Matlin et al., 1982; Marsh and Helenius, 1989; Martin and Helenius, 1991). This inhibition appeared to be at a stage beyond viral adsorption, because cells that were incubated with virus in the presence of ammonium chloride but grown in medium without ammonium chloride were efficiently infected (data not shown). This is consistent with the finding that ammonium chloride does not affect virus binding to cells (Marsh and Helenius, 1989).

Figure 6B:
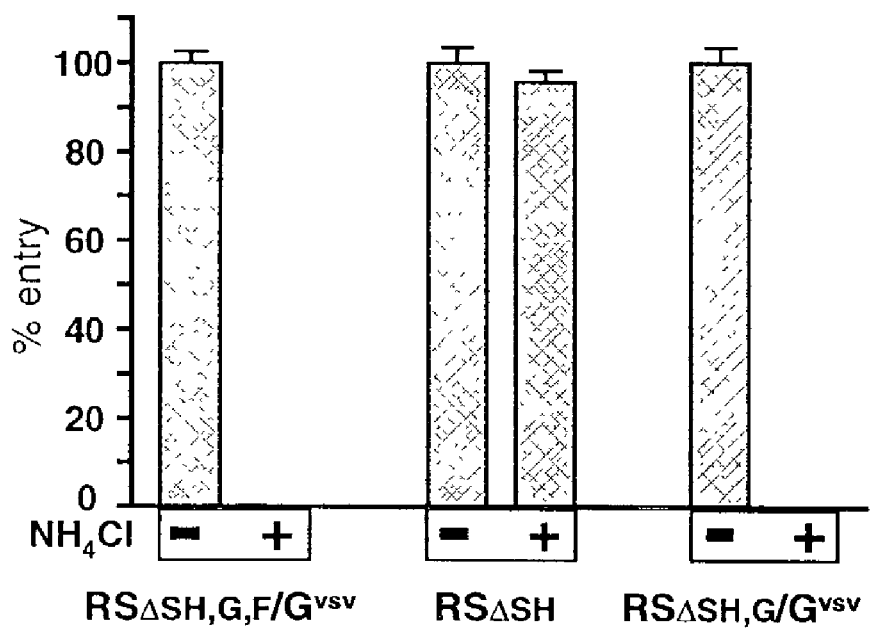
FIG. 6B shows a flow cytometry analysis. Vero cells were infected in the presence or absence of 20 mM NH$_4$Cl with viruses RSΔSH, RSΔSH,G/$G^{vsv}$, and RSΔSH,G,F/$G^{vsv}$. After infection, cells were washed and further incubated maintaining the NH$_4$Cl concentrations used during infection. At 20 hours postinfection, samples were trypsinized, fixed with paraformaldehyde and analyzed by flow cytometry. Bars represent the number of GFP expressing cells in the absence (−) or presence (+) of NH$_4$Cl, relative to the number of GFP expressing cells in the absence of NH$_4$Cl× 100%. Error bars are standard deviation from the mean of duplicate samples.

To determine whether replacement of the SH, G, and F open reading frames with that of $G^{vsv}$ altered the entry pathway from a pH-independent to a pH-dependent mode, the effects of ammonium chloride on entry of virus RSΔSH,G,F/$G^{vsv}$ were compared to that of virus RSΔSH which contains the homologous HRSV G and F proteins (FIG. 6B). Virus RSΔSH,G/$G^{vsv}$ containing two fusion-competent glycoproteins (HRSV F and $G^{vsv}$) was also included in this experiment. Vero cells were infected at a multiplicity of 1. At 20 hours postinfection, cells were trypsinized, resuspended in PBS, and pelleted in a microfuge. The cells were resuspended in 4% paraformaldehyde, and incubated for 20 min with agitation. The cells were then pelleted, resuspended in PBS, and analyzed in an FACSCalibur flow cytometer (Becton Dickinson) using 500,000 events per sample. The number of cells expressing GFP in the presence of ammonium chloride was divided by the number of GFP expressing cells in the absence of ammonium chloride and multiplied by 100% to calculate relative entry.

Infectivity of RSΔSH,G,F/$G^{vsv}$ was blocked by 20 mM ammonium chloride as above. In contrast, entry of the RSΔSH virus was unaffected, consistent with previous reports and confirming that RSΔSH and RSΔSH,G,F/G$^{vsv}$ utilize different entry pathways. Infectivity of engineered virus RSΔSH,G/G$^{vsv}$ was also severely inhibited by ammonium chloride (FIG. 6B). A similar level of inhibition of RSΔSH,G/G$^{vsv}$ infectivity was observed by immunofluorescence in both Vero and HEp-2 cells (data not shown). Apparently, despite the fact that F function was not affected by ammonium chloride (FIG. 6B, virus RSΔSH), the F protein was unable to mediate infectivity in the presence of G$^{vsv}$ in either Vero or HEp-2 cells.

EXAMPLE 9

Replication of the Engineered Viruses In Vero and Hep-2 Cells

To assess the ability of the engineered viruses to replicate and transmit in cell culture, multi-step growth curves were generated in two different cell types, Vero and HEp-2. These are cell types commonly used for in vitro HRSV studies; however, the glycoprotein requirements for HRSV infectivity in these cell types differ in that G-deleted viruses grow efficiently in Vero cells but are substantially restricted in HEp-2 cells (Karron et al., 1997; Teng et al., 2001).

Growth Curve Assay

For each virus, a series of 60 mm dishes of Vero and HEp-2 cells were infected at a multiplicity of 0.1. After virus adsorption, cells were washed once with growth medium. At 0 hours postinfection and 24 hour intervals for four (Vero) or five (HEp-2) days, supernatant and cells were harvested separately from one dish of each series, and stored at −80° C. Samples were titered by TCID$_{50}$ (using 96 well plates with 10-fold dilution series with 12 replicate wells for each dilution). GFP expression was scored at 6 days postinfection. In the case of virus A2, cells were fixed with paraformaldehyde, incubated with a mixture of anti-G and anti-F antibodies followed by a secondary antibody with a fluorescent conjugate, and scored with a fluorescence microscope.

To test whether GFP expression correlated with replicating engineered virus, plaque assays of virus RSΔSH,G,F/G$^{vsv}$ were first scored for GFP expression, then fixed and scored for G$^{vsv}$ expression via antibodies using standard plaque assay technique. Marked plaques expressing GFP overlapped precisely with plaques identified via G$^{vsv}$ (data not shown). The results of scoring TCID$_{50}$ plates of virus RSΔSH,G/G$^{vsv}$ were compared with GFP expression, or compared with expression of viral antigens (i.e. G$^{vsv}$ or F) after fixation and incubation with anti-VSIV G or anti-F antibodies. Detection based on GFP, G$^{vsv}$, or F yielded identical scores, indicating that scoring on the basis of GFP was an accurate indicator of viral replication and that comparing scores based on GFP and viral antigens detected via immunofluorescence was valid. Log TCID$_{50}$ scores of the engineered viruses were compared. To determine total virus titers, supernatant and cell-derived titers were combined.

Results

Vero and HEp-2 cells were infected with each of the engineered viruses at a multiplicity of 0.1, and replication compared to that of the prototype A2 strain. Cells and supernatants were harvested separately to determine the degree to which the different viruses remain cell-associated. Titers were determined by TCID$_{50}$, in which virus A2 was scored by immunofluorescence with a combination of anti-G/anti-F antibodies and the engineered viruses were scored using GFP expression as described above.

Figure 7A:
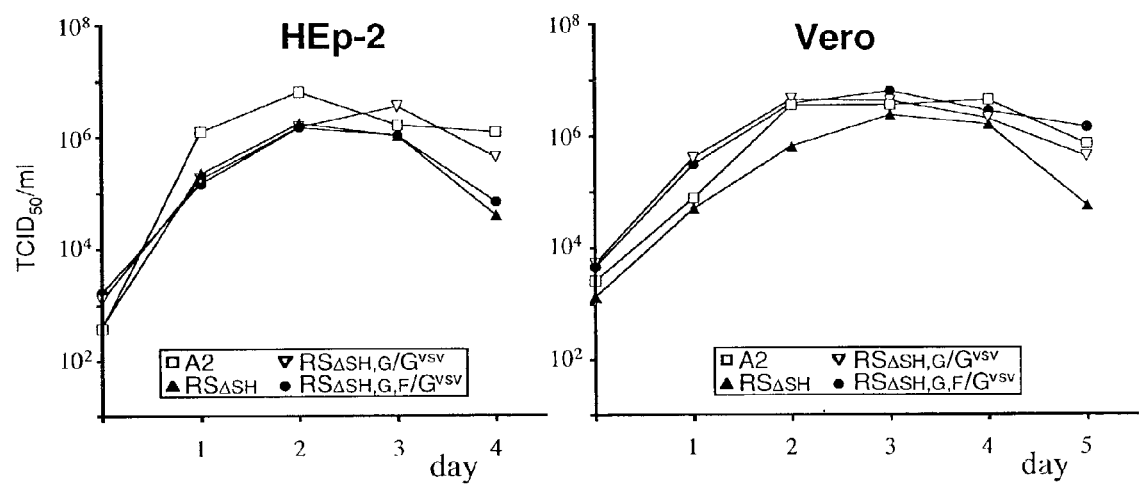
FIG. 7A shows multi-step growth curve analysis of the engineered viruses in HEp-2 and Vero cells. The engineered viruses and prototype virus A2 were used to infect Vero and HEp-2 cells at a multiplicity of 0.1. Cells and supernatants were harvested at 1 day intervals and titered by TCID$_{50}$ on the basis of GFP expression (engineered viruses) or indirect immunofluorescence (A2). Data points represent the combined titer of supernatant and cell-derived virus (total virus growth curves).

In either Vero or HEp-2 cells, the RSΔSH virus replicated to levels only slightly lower than those of wt A2 (FIG. 7A). This was consistent with previous findings that absence of SH has only a marginal effect on replication of HRSV in cell culture (Bukreyev et al., 1997; Techaarpornkul et al., 2001). The viruses RSΔSH,G/G$^{vsv}$ and RSΔSH,G,F/G$^{vsv}$ replicated to levels that were very similar to the A2 virus (FIG. 7A). In Vero cells, onset of RSΔSH,G,F/G$^{vsv}$ and RSΔSH,G/G$^{vsv}$ progeny virus production appeared somewhat accelerated compared to A2, whereas in HEp-2 the opposite was observed. Overall, despite the differences in the content of proteins involved in infectivity and the mode of virus entry, relative replication levels between all viruses were similar in both cell types tested.

Figure 7B:
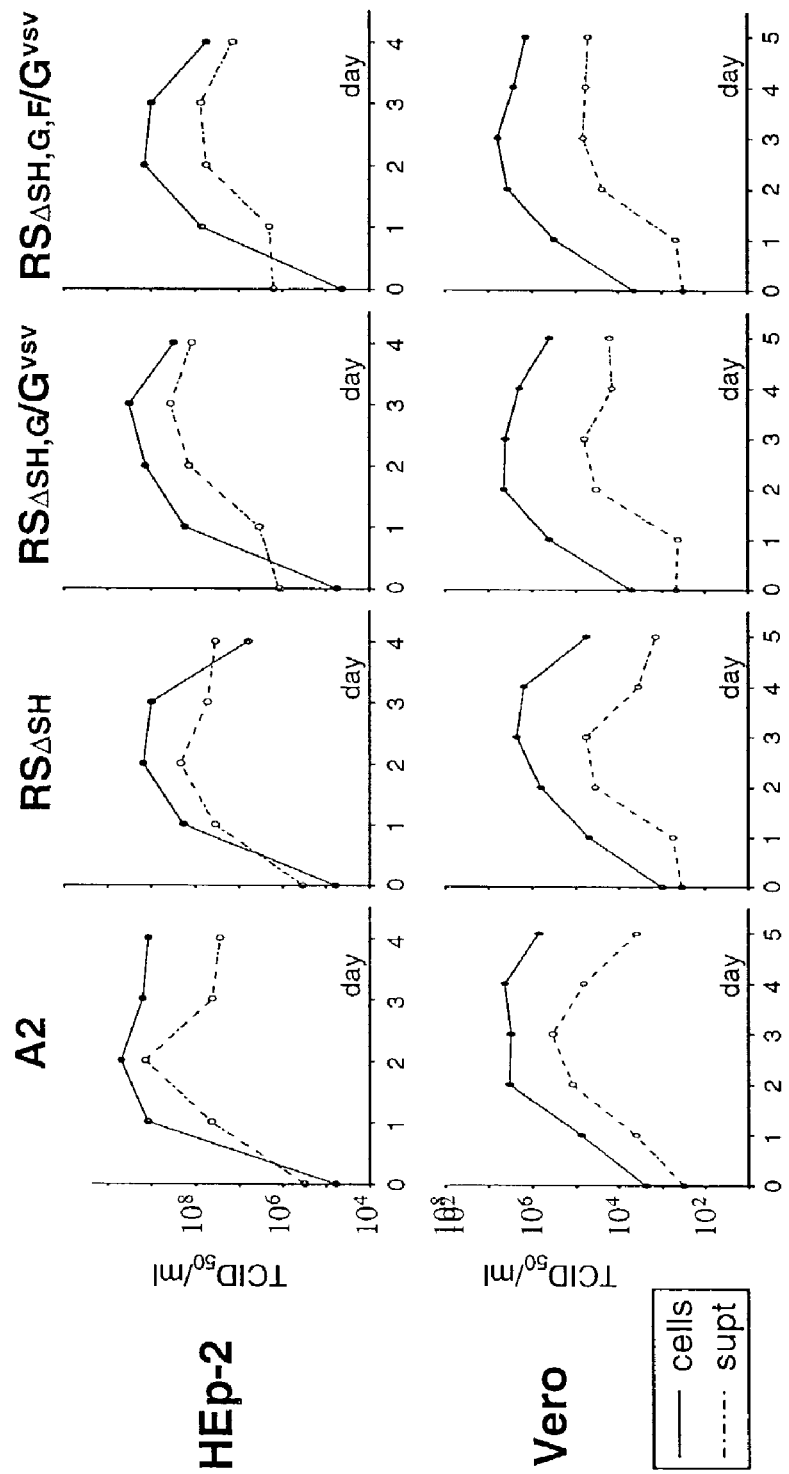
FIG. 7B compares supernatant-derived (dashed lines) and cell-derived (solid lines) virus titers from Vero and HEp-2 cells.

To examine whether the absence of HRSV glycoproteins or the presence of G$^{vsv}$ had an effect on the degree to which the engineered viruses remained cell-associated, titers determined from supernatant and cells were compared. In both Vero and HEp-2 cells, over 90% of infectivity of virus A2 was detected in the cell-associated fraction (FIG. 7B). The ratio of supernatant vs cell-associated virus observed with wt A2 virus was similar to previous reports, where the majority of infectious HRSV remained associated with Vero and Hela cells (Levine and Hamilton, 1969; Roberts et al., 1995). With the engineered viruses, no significant changes were observed in either Vero or HEp-2 cells in the ratio of cell-associated to non cell-associated virus, indicating that neither absence of the various RS glycoproteins nor presence of the G$^{vsv}$ protein significantly altered the proportion of virus released to the supernatant.

EXAMPLE 10

Filamentous Structures Form at the Cell Surface Even When the SH, G, and F Proteins are Replaced with G$^{vsv}$ Previous work has shown that human respiratory syncytial virus infection induces the formation of relatively large, cell-associated filaments at the plasma membrane in various cell types, and that the G and F proteins target to these filaments (Bächi and Howe, 1973; Fuchs and Bächi, 1975; Faulkner et al., 1976; Parry et al., 1979; Roberts et al., 1994; Buchholz et al., 2000; Stope et al., 2001). These observations appear to be in agreement with the findings that human respiratory syncytial virus infectivity is predominantly cell-associated, and that the majority of infectivity is lost after passage through 0.45 μm filters (Paccaud and Jacquier, 1970; Roberts and Wertz, 1995).

Figure 8:
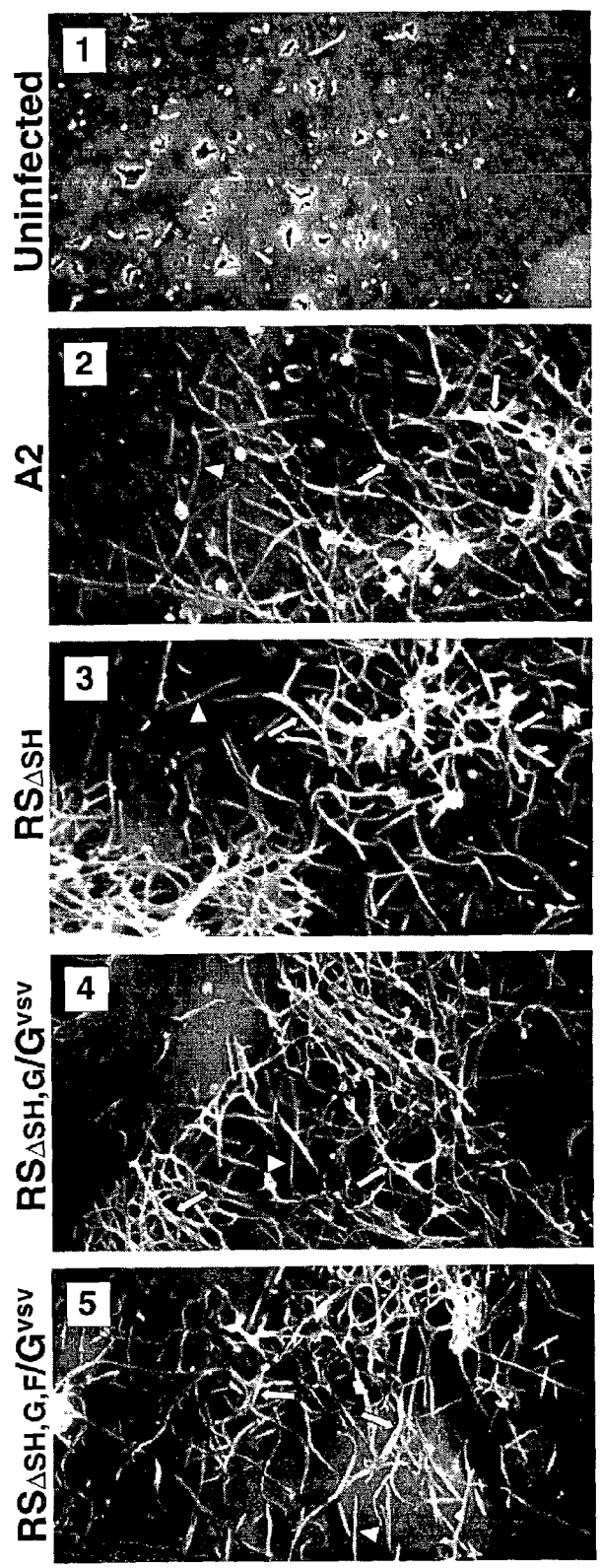
FIG. 8 shows scanning electron microscopy (SEM) analysis of the surface of virus-infected cells. Vero cells infected with the engineered viruses (panels 3 to 5) and virus A2 (panel 2), as well as uninfected Vero cells (panel 1), were fixed and processed for SEM at 26 hours postinfection, and photographed at 5000× magnification. Single filaments (triangles) as well as bundles of filaments (arrows) are indicated. Size bar: 2 μm.

To determine the effect of the absence of the human respiratory syncytial virus membrane glycoproteins on virion morphology, the surface of infected Vero cells was examined by scanning electron microscopy (FIG. 8). Vero cells infected at a multiplicity of 2 were fixed at 26 hours postinfection for 1 hour in 2.5% glutaraldehyde/0.1 M cacodylate at 25° C., followed by three washing steps in 0.1 M cacodylate buffer and immersion in 1% osmium tetroxide/0.1 M cacodylate buffer for 1 hour. Cells were rinsed three times in cacodylate buffer and once in distilled water, then dehydrated with ethanol and hexamethyldisilizane. Samples were air dried overnight, coated with gold, and analyzed on an ISI-SX-40 scanning electron microscope (International Scientific Instruments, Inc.).

In agreement with previous observations, single filaments and bundles of filaments were detected abundantly at the surface of virus A2 infected cells (FIG. 8, panel 2). Also, areas were observed where filament bundles branched off to connect to neighboring bundles, giving the appearance of a dense, highly interconnected network of filaments. Despite the variability in size and appearance (1 to 10 µm), the length of these filaments exceeded the length of microvilli (<1 µm) observed at the surface of uninfected Vero cells (FIG. 8, panel 1). Examination of the surface of cells infected by the engineered viruses revealed that in the absence of one, two, or all three of the HRSV transmembrane glycoproteins (FIG. 8, panels 3, 4, and 5 respectively), an abundance of viral filaments with a similar range in size and appearance were detected. Thus, while previous work showed that the human respiratory syncytial virus G and F proteins concentrate in virus-induced filaments at the cell surface, neither the SH, G, nor the F protein appears to be essential for their formation, with the possible exception of the F protein cytoplasmic tail domain.

EXAMPLE 11

Chimeric Glycoprotein $G^{vsv}$ Concentrates in Filamentous Structures at the Cell Surface To determine whether, as previously reported for the human respiratory syncytial virus G and F proteins, chimeric glycoprotein $G^{vsv}$ targeted to cell surface-associated filaments, virally infected cells were examined by immunofluorescence. Vero cells infected with the engineered viruses or virus A2 at low multiplicity were fixed with freshly dissolved 4% paraformaldehyde at 22 hours postinfection and incubated with anti-HRSV G or F, or anti-VSIV G antibodies. Samples were examined simultaneously for GFP and glycoprotein expression by confocal microscopy (FIG. 9A).

Figure 9A:
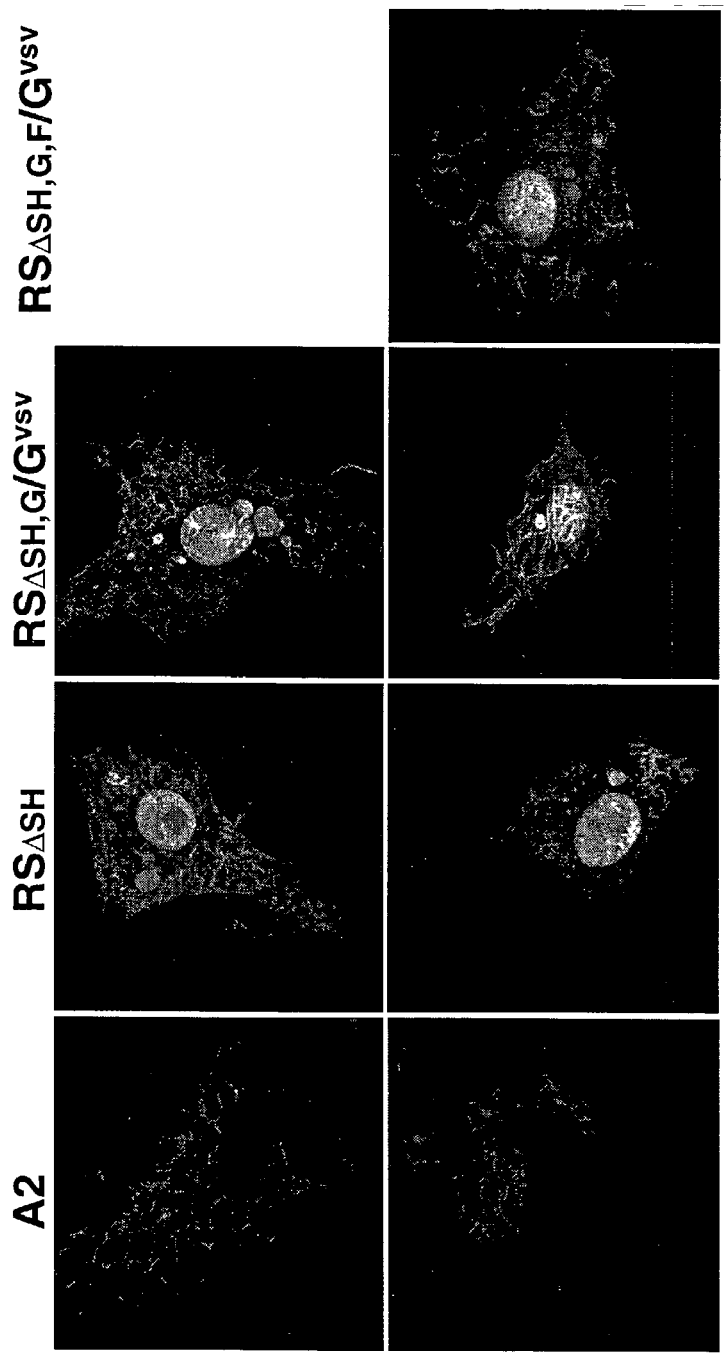
FIG. 9A shows cell surface localization of the $G^{VSV}$ protein and HRSV G and F proteins in virus infected cells by confocal microscopy. Vero cells were infected with the engineered viruses or virus A2 and fixed with freshly dissolved 4% paraformaldehyde at 22 hours post infection. G, F, and GVSV proteins were detected by incubation with anti-VSIV G (αVSIV-G) anti-HRSV G (αHRSV-G) or anti-HRSV F (αHRSV-F) antibodies, followed by incubation with an alexa-594 conjugated secondary antibody. A2-infected cells were, in addition, incubated with Hoechst stain to visualize nuclei (panels 1 and 4). Images were generated by sequential scanning for GFP expression or Hoechst stain and expression of viral antigens (G, F, $G^{VSV}$) (color not shown). Size bar: 20 μm.

As expected, GFP expression was detected in cells infected with the engineered viruses, both in the cytoplasm and in the nucleus (FIG. 9A, panels 2, 3, 5, 6, and 7). Virus A2 infected cells, which lack GFP expression, were incubated with Hoechst stain to visualize nuclei (FIG. 9A, panels 1 and 4). Both the F, G, and $G^{vsv}$ proteins concentrated in filamentous structures at or near the cell surface. No differences were observed in the morphology of the filaments between any of the engineered viruses and virus A2. In each case, the filaments were heterogeneous in appearance, ranging from discrete rods of up to 10 µm in length to dense clusters of filaments of highly variable lengths in parallel or criss-cross arrangements. These filaments likely correspond to the aggregates or bundles of filaments observed by scanning electron microscopy (FIG. 8); however, this is difficult to determine due to significant differences between the two techniques in sample treatment and visualization.

Figure 9B:
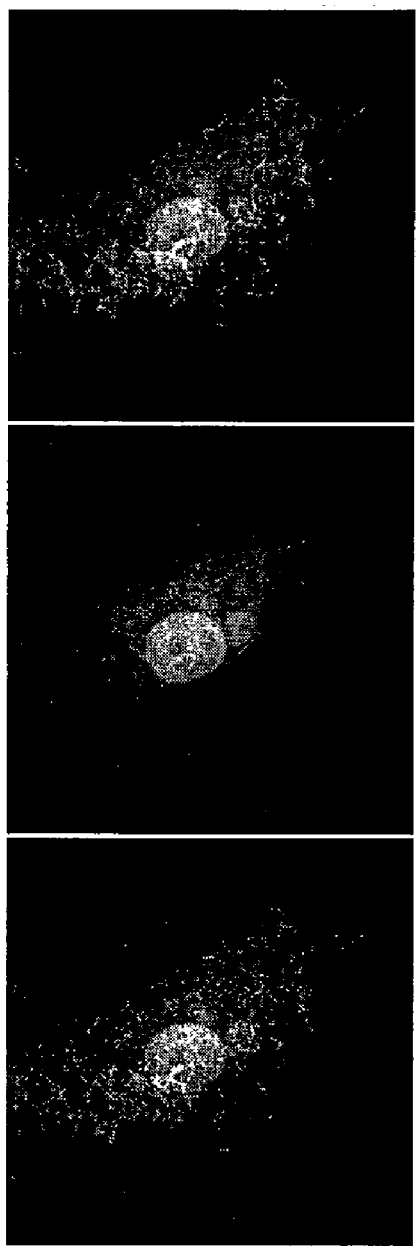
FIG. 9B shows double antibody for dual detection of F and GVSV proteins. Vero cells infected with virus RSΔSH, G/$G^{VSV}$ were fixed as above and incubated with anti HRSV F and anti-VSIV G antibodies simultaneously. The F protein was visualized with an alexa-594 conjugated antibody, $G^{VSV}$ with an alexa-350 conjugated antibody. Images were generated by sequential scanning for GFP expression, F expression, and $G^{VSV}$ expression (color not shown). Panel 3 is a merged image of panels 1 and 2.

To examine whether the $G^{vsv}$ protein would target to the same locations as the authentic HRSV F protein, cells infected with virus RSΔSH,G/$G^{vsv}$ were similarly fixed, incubated with anti-F and anti-VSIV G antibodies simultaneously, and visualized with a red or blue fluorescent conjugate respectively (FIG. 9B, panels 1 and 2). Merging of the images revealed that the $G^{vsv}$ and HRSV F proteins co-localized in filamentous structures at the surface of infected cells (FIG. 9B, panel 3). Together these data show that $G^{vsv}$ was efficiently targeted to viral-induced filaments. Whether the F cytoplasmic tail domain is required for the observed targeting remains to be determined.

EXAMPLE 12

Replacing all Three RSV Glycoproteins Genes with Baculovirus GP64 Gene

In an approach identical to the one described for incorporation of $G^{vsv}$ into an human respiratory syncytial virus lacking the SH, G, and F ORFs, this example provides an engineered human respiratory syncytial virus that lacks SH, G, and F open reading frames and carries instead a chimeric protein based on the *Autographa californica* multicapsid nucleopolyhedrovirus (AcMNPV) GP64 protein. AcMNPV is an insect virus that belongs to the Baculoviridae family. The GP64 protein is a type I, trimeric membrane glycoprotein that has the capacity to fuse lipid membranes (Blissard and Wenz, 1992; Oomens et al., 1995). In addition to membrane fusion, GP64 provides attachment as well as virus exit functions for baculo Budded Virus (BV) virions and hence plays a critical role in viral transmission (Volkman and Goldsmith, 1985; Monsma et al., 1996; Oomens and Blissard, 1999; Hefferon et al., 1999). In contrast to VSV G, no reports of complementation of unrelated viruses by GP64 exist. Moreover, synthesis of functional GP64 has only been demonstrated under insect cell physiological conditions (28° C., pH 6.0).

Interestingly however, a low but significant level of homology was described between GP64 and the envelope protein of Thogoto (THO) and Dhori (DHO), two viruses from the Orthomyxoviridae which can replicate in both ticks and vertebrates (Morse et al., 1992). In contrast to HRSV, in which the F protein mediates pH-independent fusion at the plasma membrane, GP64 mediates entry via receptor-mediated endocytosis in which a low pH activation step is required (Volkman and Goldsmith, 1985); this step can be blocked by the lysosomotropic agent ammonium chloride (Hefferon et al, 1999). In contrast; entry of human respiratory syncytial virus is not affected by the same compound (Srinivasakumar et al., 1991).

For construction of a GP64/HRSV F chimeric protein, the cytoplasmic tail domain (CTD) of GP64 (amino acids 506 to 512) was replaced with that of HRSV F (amino acids 553–574). However, syncytium formation assays indicated that a GP64 protein lacking its homologous CTD and containing the full predicted CTD of HRSV F was expressed at the cell surface but compromised in its ability to fuse membranes. Therefore, a GP64 chimeric protein carrying only the C-terminal half of the human respiratory syncytial virus F CTD (amino acids 563 to 574) was constructed, and the resulting chimeric protein was named $G^{bac}$. Exposure to low pH triggered $G^{bac}$ to induce a level of syncytium formation similar to that of an authentic GP64 protein, hence this chimeric protein was used for the construction of engineered human respiratory syncytial virus.

From the prototype human respiratory syncytial virus A2 strain, the ORFs of the SH, G and and F genes were deleted and replaced as follows. The SH ORF was replaced with that of marker protein β-glucuronidase (GUS); the open reading frame of the human respiratory syncytial virus G gene was replaced with that of chimeric glycoprotein $G^{bac}$; and the open reading frame of the F gene was replaced with that of the green fluorescent protein (GFP). These engineered constructs thus differed from previously reported deletion viruses in that each deleted gene was replaced and intergenic regions, gene start, and gene end sequences throughout the genomes remained unaltered, in order to maintain the overall sequential transcriptional control program as found in a wild type HRSV. Infectious viruse was recovered from this cDNA, and designated RSΔSH,G,F/$G^{bac}$.

Protein Expression By Virus RSΔSH,G,F/$G^{bac}$

Transmembrane glycoprotein expression was examined by immunofluorescence. Vero cells infected with virus RSΔSH,G,F/$G^{bac}$ were fixed with methanol, incubated with antibodies against the HRSV G or F proteins (L9 and MAb19 respectively) or against the GP64 protein (AcV5), and visualized using a secondary antibody carrying a fluorescent conjugate. In cells infected with virus RSΔSH,G,F/$G^{bac}$, neither the human respiratory syncytial virus G nor F proteins were detected; instead the $G^{bac}$ protein was detected. In cells infected with viruses RSΔSH and A2, which carry wt human respiratory syncytial virus G and F genes and no heterologous glycoprotein ORFs, both human respiratory syncytial virus G and F proteins were expressed, but not $G^{bac}$. These results were in agreement with the genome content of each of the viruses, and the only transmembrane glycoprotein expressed in virus RSΔSH,G,F/$G^{bac}$ was chimeric protein $G^{bac}$.

Analysis of $G^{bac}$ Function

AcMNPV replicates in the nucleus of its host cell, and early viral genes are recognized and transcribed by the host RNA polymerase II. As a consequence, many early gene products can be efficiently expressed from CMV promoters in commercial expression vectors. Plasmids containing the GP64 chimeric proteins with either the full or the C-terminal half ($G^{bac}$) of the HRSV F cytoplasmic tail domain were transfected into Vero and HEp-2 cells, and the cells were subjected to syncytium formation assay at 24 hour postransfection. $G^{bac}$ and an authentic GP64 construct used for comparison induced massive syncytium formation, whereas the chimeric protein carrying the full version of the F cytoplasmic tail domain displayed only rare formation of syncytia. Cells infected with virus RSΔSH,G,F/$G^{bac}$ also displayed extensive syncytium formation, indicating that $G^{bac}$ in the context of an engineered HRSV was fusion-competent.

Infectivity of RSΔSH,G,F/$G^{bac}$ is Neutralized by $G^{bac}$ Specific Antibodies To determine whether infectivity of RSΔSH,G,F/$G^{bac}$ virions was mediated by $G^{bac}$, the effect of anti-GP64 antibodies on the infectivity of RSΔSH,G,F/$G^{bac}$ to Vero cells was examined. RSΔSH,G,F/$G^{bac}$ was pre-treated with a neutralizing anti-GP64 Ab named AcV1 or with a non-neutralizing anti-GP64 Ab named AcV5 (Hohmann and Faulkner, 1983), and then examined for its ability to infect Vero cells. Infectivity of RSΔSH,G,F/$G^{bac}$ was greatly impaired by AcV1 but not by AcV5.

Virus RSΔSH,G,F/$G^{bac}$ Utilizes an Altered Entry Mechanism

AcMNPV BV virions enter via endocytosis, in which acidification of endosomes triggers the GP64 protein to induce virus-cell membrane fusion, an event required for entry of the nucleocapsid. This endocytic entry pathway can be blocked with compounds such as ammonium chloride that buffer the endosomal pH and thus prevent the acidification that induces virus-cell membrane fusion. In contrast to AcMNPV, human respiratory syncytial virus is believed to enter at the plasma membrane in a pH-independent manner, and it was shown previously that entry and replication of a wt human respiratory syncytial virus were not affected by ammonium chloride. Whether entry of virus RSΔSH,G,F/$G^{bac}$ was sensitive to ammonium chloride was examined by infecting Vero cells in the presence of ammonium chloride. A concentration of 20 mM ammonium chloride led to nearly complete inhibition of RSΔSH,G,F/$G^{bac}$ infectivity, while infectivity of virus RSΔSH, which contains the homologous human respiratory syncytial virus G and F proteins, was unaffected. This indicated that replacement of the SH, G, and F ORFs with that of $G^{bac}$ altered the entry pathway from a pH-independent to a pH-dependent mode.

Replication of Virus RSΔSH,G,F/$G^{bac}$ In Vero and Hep-2 Cells

To assess the ability of virus RSΔSH,G,F/$G^{bac}$ to replicate and transmit in cell culture, multi-step growth curves were generated in two different cell types, Vero and HEp-2. These are cell types commonly used for in vitro HRSV studies; however, the glycoprotein requirements for HRSV infectivity in these cell types differ in that G-deleted viruses grow efficiently in Vero cells but are substantially restricted in HEp-2 cells (Karron et al., 1997; Teng et al., 2001). The two cell types were infected with each of the engineered viruses at a multiplicity of 0.1, and replication was compared to an engineered virus containing the homologous HRSV G and F proteins and to that of the prototype A2 strain. Cells and supernatants were harvested separately to determine the degree to which the different viruses remain cell-associated. Titers were determined by $TCID_{50}$ in which virus A2 was scored by immunofluorescence with a combination of anti-G/anti-F antibodies and the engineered viruses were scored using GFP expression as described above.

In either Vero or HEp-2 cells, the RSΔSH virus replicated to levels only slightly lower than those of wt A2. This was consistent with previous findings that absence of SH has only a marginal effect on replication of HRSV in cell culture. In Vero cells, virus RSΔSH,G,F/$G^{bac}$ replicated to levels similar to those of viruses RSΔSH and A2. In HEp-2 cells, virus RSΔSH,G,F/$G^{bac}$ replicated to levels approximately 100-fold lower.

Figure 10:
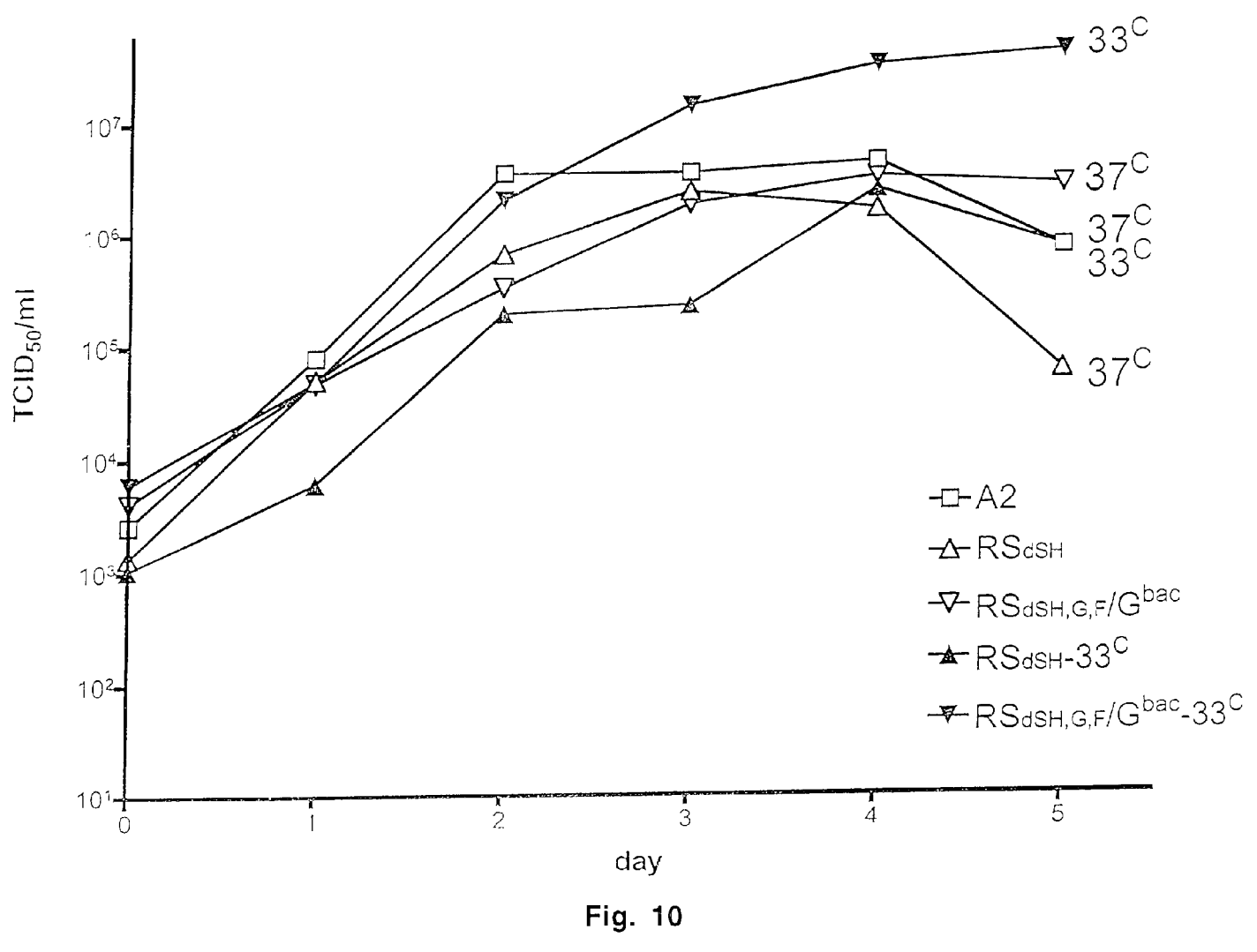
Figure 11:
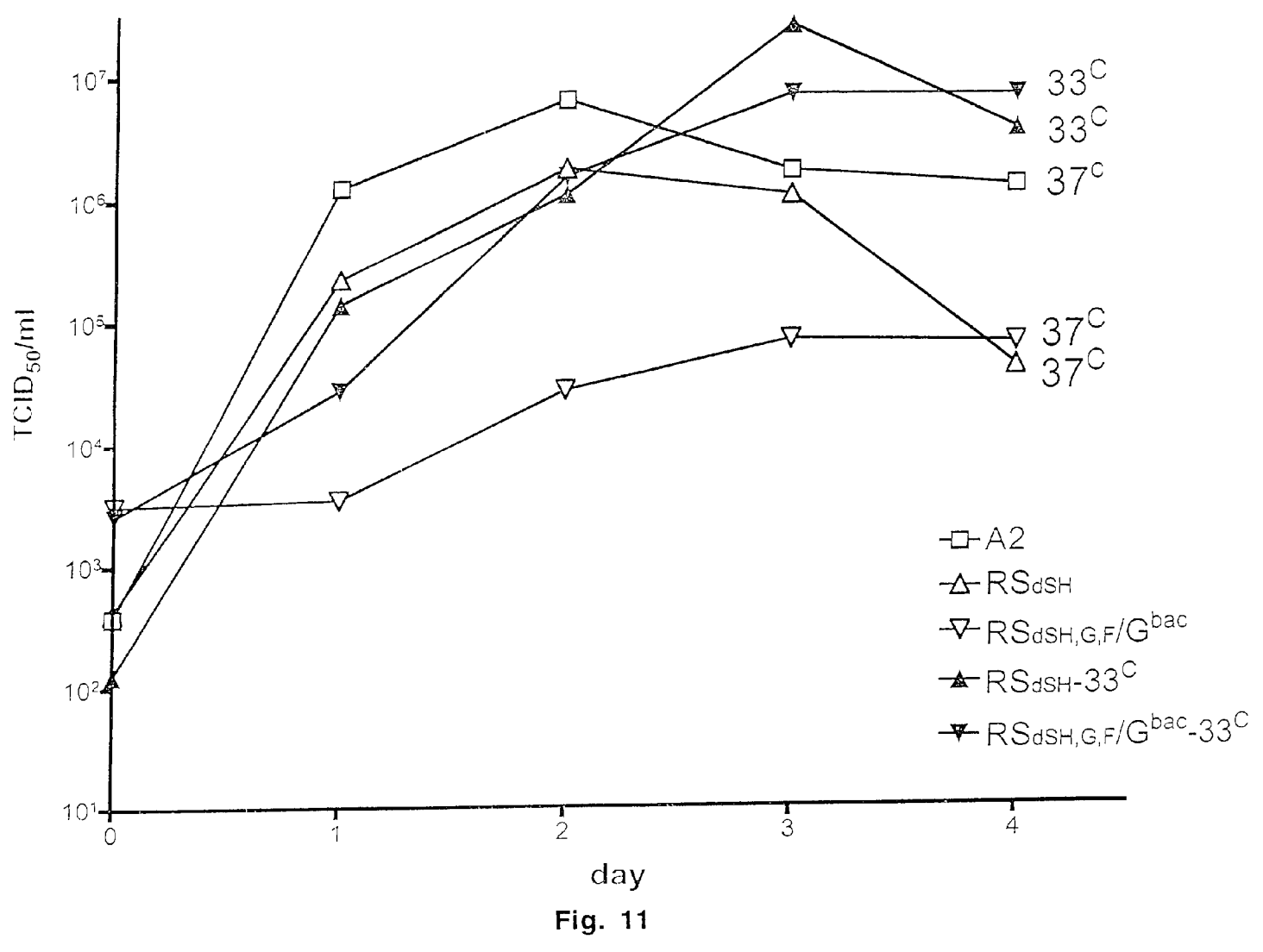

Because the physiological temperature used to cultivate insect viruses and cells is lower (28° C.), and GP64-derived $G^{bac}$ may misfold at higher temperatures, growth of RSΔSH,G,F/$G^{bac}$ at a reduced temperature was also examined. In both Vero and HEp-2 cells, replication of RSΔSH,G,F/$G^{bac}$ significantly improved when temperature was lowered to 33° C., while growth of RSΔSH remained unchanged. In Vero cells at 33° C., virus RSΔSH,G,F/$G^{bac}$ grew very efficiently as the yield of infectious virus was 10-fold higher than that of an A2 virus (FIGS. 10–11).

To examine whether the absence of human respiratory syncytial virus glycoproteins or the presence of $G^{bac}$ had an effect on the degree to which the engineered viruses remained cell-associated, titers determined from supernatant and cells were compared. In both Vero and HEp-2 cells, over 90% of infectivity of virus A2 was detected in the cell-associated fraction. The ratio of supernatant vs cell-associated virus observed with wt A2 virus was similar to previous reports where the majority of infectious human respiratory syncytial virus remained associated with Vero and Hela cells. With engineered virus RSΔSH,G,F/$G^{bac}$, no significant changes were observed in either Vero or HEp-2 cells in the ratio of cell-associated to non cell-associated virus, indicating that neither absence of the various human respiratory syncytial virus glycoproteins nor presence of the $G^{bac}$ protein significantly altered the proportion of virus released to the supernatant.

The above results indicate that transmission of respiratory syncytial viruses lacking the attachment and fusion proteins can be achieved by including a diverse group of heterologous unrelated singly-operating entry/exit proteins coupled to the respiratory syncytial virus F cytoplasmic tail domain.

EXAMPLE 13

Development of Multipurpose Vaccine

The strategy of providing glycoproteins in trans to generate replication-competent but transmission-deficient human respiratory syncytial viruses can be applied for the generation of multipurpose vaccines. Viral glycoprotein epitopes or domains from any disease-causing virus can be included in the genome of a transmission-deficient human respiratory syncytial virus. In this manner, human respiratory syncytial virus viruses can be engineered that are infectious and will replicate and abundantly express a given epitope within an infected cell, yet will not spread to neighboring cells at the risk of causing disease symptoms.

To generate the replication-competent but transmission-deficient human respiratory syncytial viruses requires cell lines that stably express the complementing proteins so that the glycoproteins can be provided in trans. GP64 was efficiently expressed from a nuclear promoter in Vero cells by transient transfection, and it did not exhibit toxicity to these cells. These features indicate good potential for the production of a cell line constitutively expressing GP64. Combined with the fact that high viral yields are produced in the presence of GP64, and that RS virus does not efficiently shut down its host cell metabolism, this indicates excellent potential for providing GP64 in trans to a virus lacking any transmembrane glycoprotein.

Cell lines constitutively expressing $G^{bac}$ were generated. This was done by transfecting Vero 76 cells with a plasmid expressing the $G^{bac}$ protein and a neomycin-resistance protein. After selection with G418 sulfate, colonies were isolated and screened for expression of $G^{bac}$ using antibody AcV5. A number of colonies were found positive, and subsequently subcloned two more times to isolate clonal lines that stably express $G^{bac}$. Currently, approximately 6 lines have been established that are maintained at 33° C., and constitutively express $G^{bac}$ as determined by immunofluorescence. These lines are being used to generate transmission-deficient human respiratory syncytial viruses by providing protein $G^{bac}$ in trans during the virus recovery process. Supernatants from the initial transfection can be passaged onto cells expressing $G^{bac}$, and recovered virus can be assessed for its rate of transmission in Vero cells.

Besides GP64, any viral glycoprotein that can be expressed from the nucleus of human respiratory syncytial virus permissive cells can be used to generate stably-expressing cell lines, and to produce engineered human respiratory syncytial virus particles that transiently carry a given viral protein in their envelope. Such strategy may be useful when at the same time specific cell-type targeting is pursued and expression of the targeting protein within the infected cell is not desired.

Production of sufficient quantities of respiratory syncytial virus vaccine candidates is problematic due to low yields and instability of the virion. However, increased yield of infectious particles by the engineered RSΔSH,G,F/$G^{bac}$ will help overcome this problem. At 33° C. in Vero cells, RSΔSH,G,F/$G^{bac}$ replicated to levels exceeding those of a wt respiratory syncytial virus (approximately 10-fold higher). In addition, VSV G has demonstrated potential to increase stability and viral yields when provided to retroviruses. Therefore, both VSV G and GP64 may confer to the respiratory syncytial virion increased stability.

Furthermore, G-deleted viruses reported by other groups replicate efficiently only in one cell type (Vero cells). In contrast, the growth of engineered respiratory syncytial virus containing the $G^{vsv}$ or $G^{bac}$ protein disclosed herein is not limited to only one cell type, thereby further enhancing their potential in producing large quantities of respiratory syncytial virus vaccine candidates.

The following references are cited herein:
Anderson et al. 1992. Polylactosaminoglycan modification of the respiratory syncytial virus small hydrophobic (SH) protein: a conserved feature among human and bovine respiratory syncytial viruses. *Virology* 191:417–30.
Bachi and Howe. 1973. Morphogenesis and ultrastructure of respiratory syncytial virus. *J Virol* 12:1173–80.
Bachi. 1988. Direct observation of the budding and fusion of an enveloped virus by video microscopy of viable cells. *J Cell Biol* 107:1689–95.
Berthiaume et al. 1974. Comparative structure, morphogenesis and biological characteristics of the respiratory syncytial (RS) virus and the pneumonia virus of mice (PVM). *Arch Gesamte Virusforsch* 45:39–51.
Bryson et al. 1991. Ultrastructural features of lesions in bronchiolar epithelium in induced respiratory syncytial virus pneumonia of calves. *Vet Pathol* 28:293–9.
Bryson et al. 1991. Ultrastructural features of alveolar lesions in induced respiratory syncytial virus pneumonia of calves. *Vet Pathol* 28:286–92.
Buchholz et al. 1999. *J Virol* 73:251–9.
Buchholz et al. 2000. *J Virol* 74:1187–99.
Bukreyev et al. 1997. *J Virol* 71:8973–82.
Burns et al. 1993. *Proc Natl Acad Sci USA* 90:8033–7.
Collins and Wertz. 1983. *PNAS* 80:3208–12.
Collins et al. 1984. *J Virol* 49:572–8.
Collins and Wertz. 1985. *Virology* 141:283–91.
Collins et al. 1990. *J Gen Virol* 71:1571–6.
Conzelmann and Schnell. 1994. *J Virol* 68:713–9.
Couch et al. 1997. *Am J Med* 102:2–9; discussion 25–6.
Dahlberg. 1974. *Virology* 58:250–62.
Doxsey et al. 1987. *Cell* 50:453–63.
Emi et al. 1991. *J Virol* 65:1202–7.
Faulkner et al. 1976. *J Virol* 20:487–500.
Feldman et al. 1999. *J Virol* 73:6610–7.
Florkiewicz and Rose. 1984. *Science* 225:721–3.
Fuchs and Bachi. 1975. *J Ultrastruct Res* 52:114–9.
Garoff et al. 1998. *Microbiol Mol Biol Rev* 62:1171–90.
Graham et al. 2002. Respiratory syncytial virus immunobiology and pathogenesis. *Virology* 297:1–7.
Han et al. 1999. *J Infect Dis* 179:25–30.
Hardy et al. 1999. *J Virol* 73:170–6.
Helenius et al. 1982. *J Gen Virol* 58 Pt 1:47–61.
Henderson et al. 2002. *Virology* 300:244–254.
Hendricks et al. 1987. *J Gen Virol* 68:1705–14.
Huang and Wertz. 1983. *J Virol* 46:667–72.
Huang et al. 1985. *Virus Res* 2:157–73.
Jin et al. 1997. *EMBO* 16:1236–47.
Joncas et al. 1969. *Virology* 38:493–6.
Kahn et al. 1999. *Virology* 254:81–91.
Karger et al. 2001. *J Gen Virol* 82:631–40.
Karron et al. 1997. *PNAS* 94:13961–6.
Levine and Hamilton. 1969. *Arch Gesamte Virusforsch* 28:122–32.
Levine et al. 1987. *J Gen Virol* 68:2521–4.
Lyles et al. 1996. *Virology* 217:76–87.
Mangor et al. 2001. *J Virol* 75:2544–56.
Marsh and Helenius. 1989. *Adv Virus Res* 36:107–51.
Martin and Helenius. 1991. *J Virol* 65:232–44.
Martinez and Melero. 2000. *J Gen Virol* 81:2715–22.
Matlin et al. 1982. Pathway of vesicular stomatitis virus entry leading to infection. *J Mol Biol* 156:609–31.
Mebatsion et al. 1996. Budding of rabies virus particles in the absence of the spike glycoprotein. *Cell* 84:941–51.
Murphy et al. 1990. *Vaccine* 8:497–502.
Oomens and Blissard. 1999. *Virology* 254:297–314.

Paccaud and Jacquier. 1970. A respiratory syncytial virus of bovine origin. *Arch Gesamte Virusforsch* 30:327–42.
Parry et al. 1979. Pneumoviruses: the cell surface of lytically and persistently infected cells. *J Gen Virol* 44:479–91.
Pattnaik et al. 1992. *Cell* 69:1011–20.
Pringle. 1987. *Bull World Health Organ* 65:133–7.
Roberts et al. 1994. *J Virol* 68:4538–46.
Roberts et al. 1995. Respiratory syncytial virus matures at the apical surfaces of polarized epithelial cells. *J Virol* 69:2667–73.
Schmitt et al. 2002. *J Virol* 76:3952–64.
Schnell et al. 1998. *EMBO J* 17:1289–96.
Spielhofer et al. 1998. Chimeric measles viruses with a foreign envelope. *J Virol* 72:2150–9.
Srinivasakumar et al. 1991. *J Virol* 65:4063–9.
Stope et al. 2001. *J Virol* 75:9367–77.
Stott et al. 1987. *J Virol* 61:3855–61.
Sullender. 2000. *Clin Microbiol Rev* 13:1–15.
Sussman. 1995. *Biotechniques* 18:50–1.
Takimoto et al. 1998. *J Virol* 72:9747–54.
Techaarpornkul et al. 2001. *J Virol* 75:6825–34.
Teng and Collins. 1998. *J Virol* 72:5707–16.
Teng et al. 2001. *Virology* 289:283–96.
Tripp et al. 1999. *J Virol* 73:7099–107.
Varga and Braciale. 2002. *Virology* 295:203–7.
Walsh and Hruska. 1983. *J Virol* 47:171–7.
Wertz et al. 1985. *Proc Natl Acad Sci USA* 82:4075–9.
Wertz et al. 1987. Expression of the fusion protein of human respiratory syncytial virus from recombinant vaccinia virus vectors and protection of vaccinated mice. *J Virol* 61:293–301.
Wertz et al. 1989. Structure and cell surface maturation of the attachment glycoprotein of human respiratory syncytial virus in a cell line deficient in O glycosylation. *J Virol* 63:4767–76.
Whelan et al. 1995. Efficient recovery of infectious vesicular stomatitis virus entirely from cDNA clones. *PNAS* 92:8388–92.
Whitehead et al. 1999. Recombinant respiratory syncytial virus bearing a deletion of either the NS2 or SH gene is attenuated in chimpanzees. *J Virol* 73:3438–42.
Wyatt et al. 1995. Replication-deficient vaccinia virus encoding bacteriophage T7 RNA polymerase for transient gene expression in mammalian cells. *Virology* 210:202–5.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and/or specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A recombinant respiratory syncytial virus in which all of the surface glycoprotein genes encoding the attachment protein G, the fusion protein F, and the Small Hydrophobic protein SH are deleted and replaced by a gene encoding a heterologous protein that mediates cell infection and entry activity of said respiratory syncytial virus.

2. The recombinant respiratory syncytial virus of claim 1, wherein said heterologous protein includes a cytoplasmic tail domain of respiratory syncytial virus fusion protein F.

3. The recombinant respiratory syncytial virus of claim 2, wherein said heterologous protein is selected from the group consisting of the G protein of Vesicular Stomatitis Virus and the GP64 protein of baculovirus.

4. The recombinant respiratory syncytial virus of claim 1, wherein said virus further contain one or more marker genes.

5. The recombinant respiratory syncytial virus of claim 4, wherein said marker gene encodes a protein selected from the group consisting of β-glucuronidase and green fluorescent protein.

* * * * *